US009005967B2

(12) United States Patent
Yamanaka et al.

(10) Patent No.: US 9,005,967 B2
(45) Date of Patent: Apr. 14, 2015

(54) MYC VARIANTS IMPROVE INDUCED PLURIPOTENT STEM CELL GENERATION EFFICIENCY

(75) Inventors: Shinya Yamanaka, Kyoto (JP); Masato Nakagawa, Kyoto (JP)

(73) Assignee: Kyoto University, Kyoto (JP)

( * ) Notice: Subject to any disclaimer, the term of this patent is extended or adjusted under 35 U.S.C. 154(b) by 227 days.

(21) Appl. No.: 13/497,044

(22) PCT Filed: Jan. 21, 2011

(86) PCT No.: PCT/JP2011/051685

§ 371 (c)(1), (2), (4) Date: Mar. 19, 2012

(87) PCT Pub. No.: WO2011/090221

PCT Pub. Date: Jul. 28, 2011

(65) Prior Publication Data

US 2012/0276636 A1 Nov. 1, 2012

Related U.S. Application Data

(60) Provisional application No. 61/282,320, filed on Jan. 22, 2010.

(51) Int. Cl.

*C12N 5/02* (2006.01)
*C07K 14/435* (2006.01)
*C12N 5/074* (2010.01)

(52) U.S. Cl.

CPC ............ *C07K 14/435* (2013.01); *C12N 5/0696* (2013.01); *C12N 2501/603* (2013.01); *C12N 2501/608* (2013.01); *C12N 2501/605* (2013.01); *C12N 2501/602* (2013.01); *C12N 2501/604* (2013.01); *C12N 2501/606* (2013.01)

(58) Field of Classification Search

CPC ........... C12N 5/0696; C12N 2501/603; C12N 2501/604; C12N 2501/606; C12N 2501/602; C12N 2501/605; C12N 2501/608

See application file for complete search history.

(56) References Cited

U.S. PATENT DOCUMENTS

| | | | |
|---|---|---|---|
| 4,937,190 | A | 6/1990 | Palmenberg et al. |
| 2009/0227032 | A1 | 9/2009 | Yamanaka et al. |

FOREIGN PATENT DOCUMENTS

| | | | |
|---|---|---|---|
| AU | 2008/297024 | A1 | 5/2009 |
| CA | 2660123 | A1 | 4/2009 |
| CN | 101617043 | A | 12/2009 |
| EP | 2096169 | A | 9/2009 |
| JP | A 2004-121165 | A | 4/2004 |
| JP | 3602058 | B2 | 12/2004 |
| JP | A 2002-291469 | A | 6/2005 |
| KR | 2010-0075771 | A | 7/2010 |
| WO | WO 99/64565 | A2 | 12/1999 |
| WO | WO 01/62899 | A2 | 8/2001 |
| WO | WO 2007/069666 | A1 | 6/2007 |
| WO | WO 2008/118820 | A2 | 11/2008 |
| WO | WO 2009/057831 | A1 | 5/2009 |
| WO | WO 2009/057831 | A1 | 7/2009 |

OTHER PUBLICATIONS

Stadtfeld et al. Induced pluripotent stem cells generated without viral integration. Science, vol. 322. pp. 945-949.*

Gonzales et al. Generation of mouse-induced pluripotent stem cells by transient expression of a single nonviral polycistronic vector. PNAS, 2009, vol. 106, pp. 8918-8922.*

Yamanaka. Induction of pluripotent stem cells from mouse fibroblasts by four transcription factors. Cell Prolif., 2008, vol. 41 (Suppl. 1), pp. 51-56.*

Strelchenko et al. Embryonic Stem Cells from Morula, Methods in Enzymology, 2006, Vol. 418, pp. 93-108.*

Bigdeli et al. Adaptation of Human Embryonic Stem Cells to Feeder-Free and Matrix-Free Culture Conditions Directly on Plastic Surfaces. J. Biotec., 2008, vol. 133, pp. 146-153.*

Baker, M., State of the Stem Cell, Nature, doi:10.1038, published online, 2009.

Barrett, J., et al., Activation Domains of L-Myc and c-Myc Determine Their Transforming Potencies in Rat Embryo Cells, Molecular and Cellular Biology 12(7):3130-3137, 1992.

Barroso-Deljesus, A., et al., Embryonic Stem Cell-Specific miR302-367 Cluster: Human Gene Structure and Functional Characterization of Its Core Promoter, Molecular and Cellular Biology 28(21):6609-6619, 2008.

Birrer, M.J., et al., L-myc Cooperates with ras to Transform Primary Rat Embryo Fibroblasts, Molecular and Cellular Biology 8(6):2668-2673, 1988.

Blackwood, E.M., et al., Max: A Helix-Loop-Helix Zipper Protein That Forms a Sequence-Specific DNA-Binding Complex with Myc, Science 251(4998):1211-1217, 1991.

(Continued)

*Primary Examiner* — Deborah Crouch

(74) *Attorney, Agent, or Firm* — Knobbe, Martens, Olson & Bear LLP

(57) ABSTRACT

The present invention provides a method for improving iPS cell generation efficiency, which comprises a step of introducing a Myc variant having the following features: (1) having an activity to improve iPS cell generation efficiency which is comparative to, or greater than that of c-Myc; and (2) having a transformation activity which is lower than that of c-Myc; or a nucleic acid encoding the variant, in a nuclear reprogramming step. Also, the present invention provides a method for preparing iPS cells, which comprises a step of introducing the above Myc variant or a nucleic acid encoding the variant and a combination of nuclear reprogramming factors into somatic cells. Moreover, the present invention provides iPS cells comprising the nucleic acid encoding the Myc variant which can be obtained by the above method, and a method for preparing somatic cells which comprises inducing differentiation of the iPS cells.

14 Claims, 9 Drawing Sheets

(56) References Cited

OTHER PUBLICATIONS

Brough, D.E., et al., An Essential Domain of the c-Myc Protein Interacts with a Nuclear Factor That is Also Required for E1A-Mediated Transformation, Molecular and Cellular Biology 15(3):1536-1544, 1995.

Chang, C.-W., et al., Polycistronic Lentiviral Vector for "Hit and Run" Reprogramming of Adult Skin Fibroblasts to Induced Pluripotent Stem Cells, Stem Cells 27:1042-1049, 2009.

Derossi, D., et al., The Third Helix of the Antennapedia Homeodomain Translocates Through Biological Membranes, J. Biol. Chem. 269(14):10444-10450, 1994.

Eilers, M., and R.N. Eisenman, Myc's Broad Reach, Genes & Development 22:2755-2766, 2008.

Elmquist, A., et al., VE-Cadherin-Derived Cell-Penetrating Peptide, pVEC, with Carrier Functions, Exp. Cell Res. 269:237-244, 2001.

Feng, B., Reprogramming of Fibroblasts Into Induced Pluripotent Stem Cells With Orphan Nuclear Receptor Esrrb, Nature Cell Biology 11:197-203, 2009.

Frankel, A. and C. Pabo, Cellular Uptake of the Tat Protein from Human Immunodeficiency Virus, Cell 55:1189-1193, 1988.

Fusaki, N., et al., Efficient Induction of Transgene-Free Human Pluripotent Stem Cells Using a Vector Based on Sendai Virus, an RNA Virus That Does Not Integrate Into the Host Genome, Proc. Jpn. Acad., Ser. B, 85:348-362, 2009.

Gao, C., et al., A Cell-Penetrating Peptide from a Novel pVII-pIX Phage-Displayed Random Peptide Library, Bioorganic & Medicinal Chemistry 10:40574065, 2002.

Green, M., and P.M. Loewenstein, Autonomous Functional Domains of Chemically Synthesized Human Immunodeficiency Virus Tat Trans-Activator Protein, Cell 55:1179-1188, 1988.

Hasegawa, K., Efficient Multicistronic Expression of a Transgene in Human Embryonic Stem Cells, Stem Cells 25(7), 1707-1712, 2007.

Hasegawa, K., Supplementary Figures, 2007.

Herold, S., et al., Negative Regulation of the Mammalian UV Response by Myc Through Association with Miz-1, Molecular Cell 10(3):509-521, 2002.

Hong, F.D. and G.L. Clayman, Isolation of a Peptide for Targeted Drug Delivery into Human Head and Neck Solid Tumors, Cancer Research 60:6551-6556, 2000.

Hsiao, E.C., Marking Embryonic Stem Cells with a 2A Self-Cleaving Peptide: A NKX2-5 Emerald GFP BAC Reporter, PLoS One 3(7):e2532, 2008.

Huangfu, D., et al., Induction of Pluripotent Stem Cells by Defined Factors is Greatly Improved by Small-Molecule Compounds, Nat. Biotechnol., 26(7):795-797, 2008.

Judson, R.L., Embryonic Stem Cell-Specific microRNAs Promote Induced Pluripotency, Nat. Biotechnol. 27:459-461, 2009.

Kaji, K., et al., Virus-Free Induction of Pluripotency and Subsequent Excision of Reprogramming Factors, Nature, 458:771-775, 2009.

Kano, F., et al., Reconstitution of Golgi disassembly by mitotic *Xenopus* egg extract in semi-intact MDCK cells, Methods in Molecular Biology 322:357-365, 2006.

Kim, D., Generation of Human Induced Pluripotent Stem Cells by Direct Delivery of Reprogramming Proteins, Cell Stem Cell 4(6):472-476, 2009.

Kim J.B., et al., Oct4-induced pluripotency in adult neural stem cells, Cell 136:411-419, 2009.

Kim, J.B., Pluripotent Stem Cells Induced From Adult Neural Stem Cells by Reprogramming With Two Factors, Nature 454:646-650, 2008.

Kitamura, T., Retrovirus-Mediated Gene Transfer and Expression cloning: Powerful Tools in Functional Genomics, Exp. Hematol. 31:1007-1014, 2003.

Kondo, E., et al., Highly Efficient Delivery of p16 Antitumor Peptide into Aggressive Leukemia/Lymphoma Cells Using a Novel Transporter System, Mol. Cancer Ther. 3(12):1623-1630, 2004.

Kurian, K.M., The Impact of Neural Stem Cell Biology on CNS Carcinogenesis and Tumor Types, Patholog. Res. Int. 2011, doi:10.4061/2011/685271, 2011.

Liao, J., et al., Enhanced efficiency of generating induced pluripotent stem (iPS) cells from human somatic cells by a combination of six transcription factors, Cell Research 18:600-603, 2008.

Lin, Y.Z., et al., Inhibition of Nuclear Translocation of Transcription Factor NF-kB by a Synthetic Peptide Containing a Cell Membrane-Permeable Motif and Nuclear Localization Sequence, J. Biol. Chem. 270(24):14255-14258, 1995.

Lopez, M.D., and T. Samuelsson, Early Evolution of Histone mRNA 3' End Processing, RNA 14:1-10, 2008.

Lundberg, P., et al., Cell Membrane Translocation of the N-Terminal (1-28) Part of the Prion Protein, Biochem. Biophys. Res. Commun. 299:85-90, 2002.

Lutz, W., et al., Contributions of Myc to Tumorigenesis, Biochim. Biophys. Acta. 1602:61-71, 2002.

Maherali, N., et al., "Directly Reprogrammed Fibroblasts Show Global Epigenetic Remodeling and Widespread Tissue Contribution," Cell Stem Cell 1:55-70, 2007.

Mali, P., et al., Improved Efficiency and Pace of Generating Induced Pluripotent Stem Cells From Human Adult and Fetal Fibroblasts, Stem Cells 26(8):1998-2005, 2008.

Malynn, B., et al., N-myc Can Functionally Replace c-myc in Murine Development, Cellular Growth, and Differentiation, Genes & Development 14(11):1390-1399, 2000.

Marson, A., et al., "Wnt Signaling Promotes Reprogramming of Somatic Cells to Pluripotency," Cell Stem Cell 3:132-135, 2008.

McMahon, A.P., and A., Bradley, The Wnt-1 (int-1) Proto-Oncogene Is Required for Development of a Large Region of the Mouse Brain, Cell 62:1073-1085, 1990.

Morita, S., et al., Plat-E: An Efficient and Stable System for Transient Packaging of Retroviruses, Gene Therapy 7:1063-1066, 2000.

Morris, M.C., et al., A Peptide Carrier for the Delivery of Biologically Active Proteins into Mammalian Cells, Nature Biotechnol. 19:1173-1176, 2001.

Nakagawa, M., et al., "Generation of Induced Pluripotent Stem Cells Without Myc From Mouse and Human Fibroblasts," Nature Biotechnology 26:101-106, 2008.

Nishimura, K., et al., Persistent and Stable Gene Expression by a Cytoplasmic RNA Replicon Based on a Noncytopathic Variant Sendai Virus, J. Biol. Chem., 282:27383-27391, 2007.

Oehlke, J., et al., Cellular Uptake of an Alpha-Helical Amphipathic Model Peptide with the Potential to Deliver Polar Compounds into the Cell Interior Non-Endocytically, Biochim Biophys. Acta. 1414:127-139, 1998.

Okita, K., et al., "Generation of Germline-Competent Induced Pluripotent Stem Cells," Nature 448:313-317, 2007.

Okita, K., et al., Generation of Mouse Induced Pluripotent Stem Cells Without Viral Vectors, Science 322:949-953, 2008.

Park, C.B., et al., Structure-Activity Analysis of Buforin II, a Histone H2A-Derived Antimicrobial Peptide: The Proline Hinge is Responsible for the Cell-Penetrating Ability of Buforin II, Proc. Natl. Acad. Sci. USA 97(15):8245-8250, 2000.

Park, I.H., et al., "Reprogramming of Human Somatic Cells to Pluripotency With Defined Factors," Nature 451:141-146, 2008.

Pooga, M., et al., Cell Penetration by Transportan, FASEB Journal 12:67-77, 1998.

Rousselle, C., et al., New Advances in the Transport of Doxorubicin Through the Blood-Brain Barrier by a Peptide Vector-Mediated Strategy, Molecular Pharmacology 57:679-686, 2000.

Sawada, M., et al., Cytoprotective Membrane-Permeable Peptides Designed from the Bax-Binding Domain of Ku70, Nature Cell Biol. 5:352-357, 2003.

Sawada, M., et al., Nature Cell Biology 9(4):480, 2007, Retraction.

Shi, Y., et al., A Combined Chemical and Genetic Approach for the Generation of Induced Pluripotent Stem Cells, Cell Stem Cell 2:525-528, 2008.

Shi, Y., et al., Induction of Pluripotent Stem Cells From Mouse Embryonic Fibroblasts by Oct4 and Klf4 With Small-Molecule Compounds, Cell Stem Cell 3:568-574, 2008.

Soldner, F., et al., Parkinson's Disease Patient-Derived Induced Pluripotent Stem Cells Free of Viral Reprogramming Factors, Cell 136:964-977, 2009.

(56) References Cited

OTHER PUBLICATIONS

Takahashi, K., and Yamanaka, S., "Induction of Pluripotent Stem Cells From Mouse Embryonic and Adult Fibroblast Cultures by Defined Factors," Cell 126:663-676, 2006.

Takahashi, K., et al., "Induction of Pluripotent Stem Cells From Adult Human Fibroblasts by Defined Factors," Cell 131:861-872, 2007.

Wernig, M., et al., "In Vitro Reprogramming of Fibroblasts into a Pluripotent ES-Cell-Like State," Nature 448:318-324, 2007.

Woltjen, et al., piggyback Transposition Reprograms Fibroblasts to Induced Pluripotent Stem Cells, Nature, 458:766-770, 2009.

Yu, et al., Human Induced Pluripotent Stem Cells Free of Vector and Transgene Sequences, Science 324:797-801, 2009.

Yu, J., et al., "Induced Pluripotent Stem Cell Lines Derived From Human Somatic Cells," Science 318:1917-1920, 2007.

Zhao, Y., et al., Two Supporting Factors Greatly Improve the Efficiency of Human iPSC Generation, Cell Stem Cell 3:475-479, 2008.

Zhou, H., et al., Generation of Induced Pluripotent Stem Cells Using Recombinant Proteins, Cell Stem Cell 4:381-384, 2009.

International Search Report and Written Opinion in PCT Application No. PCT/JP2011/051685 mailed on Apr. 5, 2011 in 9 pages.

Crouch et al., Multiple phenotypes associated with Myc-induced transformation of chick embryo fibroblasts can be dissociated by a basic region mutation., Nucleic Acids Research, 1996, vol. 24, No. 16, pp. 3216-32221.

Nakagawa M et al., Promotion of direct reprogramming by transformation-deficient Myc., Proc Natl Acad Sci USA, Aug. 2010, vol. 107, No. 32, pp. 14152-14157.

Sarid J et al., Evolutionary conserved regions of the human c-myc protein can be uncoupled from transforming activity, Proc Natl Acad Sci USA, Jan. 1987, vol. 84, No. 1, pp. 170-173.

* cited by examiner

Figure 10

```
Hu-c-MYC    MPLNVSFTN-----RNYDLDYDSVQPYFYCDEEENFYQQQQQSELQPPAPSEDIWKKFEL 55
Hu-N-MYC    MPSCSTSTMPGMICKNPDLEFDSLQPCFYPDEDD-FYFGGPDS----TPPGEDIWKKFEL 55
            **   : *       :* **::**:** ** **:: **     :*    ..*.*********

Hu-c-MYC    LPTPPLSPSRRSGLCSPSYVAVTPFSLRGDNDGGGGSFSTADQLEMVTELLGGDMVNQSF 115
Hu-N-MYC    LPTPPLSPSR------------------GFAEHSSEPPSWVTEMLLENELWGSPAEEDAF 97
            **********                  *  : .. . * . :: : .** *.   :::*

Hu-c-MYC    ICDPDDETFIKNIIIQDCMWSGFSAAAKL---VSEKLAS--------YQAARKDSGSPNP 164
Hu-N-MYC    GLGGLGGLTPNPVILQDCMWSGFSAREKLERAVSEKLQHGRGPPTAGSTAQSPGAGAASP 157
              .  .     : :*:**********  **    *****            *   .:*:..*

Hu-c-MYC    A-RGHSVCS----TSSLYLQDLSAAASECIDPSVVFPYPLND-SSSPKSCASQDSSAFSP 218
Hu-N-MYC    AGRGHGGAAGAGRAGAALPAELAHPAAECVDPAVVFPFPVNKREPAPVPAAPASAPAAGP 217
            * ***. .:     :.:     :*: .*:**:**:****:*:*. ..:* ..*. .:.* .*

Hu-c-MYC    SSDS--LLSSTESSP-------------QGSPEPLVLHEETPPTTSSDSEEEQEDEEE-I 262
Hu-N-MYC    AVASGAGIAAPAGAPGVAPPRPGGRQTSGGDHKALSTSGEDTLSDSDDEDDEEEDEEEEI 277
            :  *   :::. .:*             *. :.*    * . : *.*.::*:***** *

Hu-c-MYC    DVVSVEKRQAPGKR--------SESGSPSAGGHSKPPHSPLVLKRCHVSTHQHNYAAPP- 313
Hu-N-MYC    DVVTVEKRRSSSNTKAVTTFTITVRPKNAALGPGRAQSSELILKRCLPIHQQHNYAAPSP 337
            ***:****::..:          :    . :* * .:.   * *:****    :*******.

Hu-c-MYC    -STRKDYPAAKRVKLDS-VRVLR-QISNNRKCTSPRSSDTEENVKRRTHNVLERQRRNEL 370
Hu-N-MYC    YVESEDAPPQKKIKSEASPRPLKSVIPPKAKSLSPRNSDSEDSERRRNHNILERQRRNDL 397
                :* *. *::* ::  * *:  *. : *. ***.**:*:. :**.**:*******:*

Hu-c-MYC    KRSFFALRDQIPELENNEKAPKVVILKKATAYILSVQAEEQKLISEEDLLRKRREQLKHK 430
Hu-N-MYC    RSSFLTLRDHVPELVKNEKAAKVVILKKATEYVHSLQAEEHQLLLEKEKLQARQQQLLKK 457
            : **::***::*** :****.********* *: *:****::*: *:: *: *::** :*

Hu-c-MYC    LEQLRNSCA 439
Hu-N-MYC    IEHAR-TC- 464
            :*: * :*
```

MYC VARIANTS IMPROVE INDUCED PLURIPOTENT STEM CELL GENERATION EFFICIENCY

CROSS-REFERENCE TO RELATED APPLICATIONS

This application is the U.S. national phase under 35 U.S.C. §371 of International Application No. PCT/JP2011/051685, filed Jan. 21, 2011, in the English language, which claims the benefit of U.S. Provisional Patent Application No. 61/282,320, filed Jan. 22, 2010.

REFERENCE TO SEQUENCE LISTING

This application incorporates by reference the sequence listing submitted as ASCII text filed via EFS-Web on Mar. 19, 2012. The Sequence Listing is provided as a file entitled "12961225_1.TXT", created on Mar. 19, 2012 and which is approximately 4 kilobytes in size.

TECHNICAL FIELD

The present invention relates to a method for improving induced pluripotent stem cell (hereinafter referred to as "iPS cell") generation efficiency and a factor for improving iPS cell generation efficiency.

BACKGROUND ART

Mouse and human iPS cells were established recently. Takahashi and Yamanaka (Non patent literature 1) established mouse iPS cells by introducing Oct3/4, Sox2, Klf4 and c-Myc genes into fibroblasts derived from a reporter mouse in which a neomycin-resistant gene was knocked-in into the Fbx15 locus, and forcibly expressing the four genes. Okita et al. (Non-patent literature 2) prepared a transgenic mouse by integrating green fluorescent protein (GFP) and puromycin-resistant genes into the Nanog locus, forcibly expressed the above four genes in the fibroblasts derived from the transgenic mouse, and selected puromycin-resistant and GFP-positive cells, thereby successfully generated iPS cells (Nanog iPS cells) which are almost equal to embryonic stem (ES) cells in gene expression and epigenetic modification. Nanog is specifically expressed in pluripotent cells and is more limitedly expressed in pluripotent cells than Fbx15. Similar results were also reproduced by other study groups (Non-patent literatures 3 and 4). Thereafter, it was found that iPS cells can be prepared even using three genes of Oct3/4, Sox2 and Klf4, i.e. the above four genes except for c-Myc gene (Non-patent literature 5).

Moreover, Takahashi et al. (Non-patent literature 6) successfully generated human iPS cells by introducing the four genes similar to those used for generating mouse iPS cells into fibroblasts derived from human skin. On the other hand, Yu et al. (Non-patent literature 7) prepared human iPS cells using Nanog and Lin28 instead of Klf4 and c-Myc. Furthermore, Park et al. (Non-patent literature 8) prepared human iPS cells by using TERT known as a human cell-immortalizing gene and SV40 large T antigen, in addition to the four genes of Oct3/4, Sox2, Klf4, and c-Myc. As described above, it was shown that iPS cells which are comparable to ES cells in pluripotent differentiation can be prepared in human and mouse by introducing particular factors into somatic cells.

The c-Myc gene has the risk of tumor development, and therefore, no use of the gene is desirable in the induction of iPS cells that are used for clinical therapies. Since, however, iPS cell generation efficiency was reported very low when using the three genes without c-Myc (Non-patent literature 5), it has been thought that research of a factor to replace the c-Myc is important. The factor hopefully has an effect to improve iPS cell generation efficiency comparable to or greater than that of c-Myc, and has a reduced risk of tumor development.

In this connection, the present inventors have previously revealed that iPS cell generation efficiency was improved by using L-Myc instead of c-Myc in the generation of human iPS cells. In addition to iPS cell generation efficiency, L-Myc was revealed to increase surviving days of chimeric mice and decrease tumor formation (patent literatures 1 and 2).

Documents cited (the following documents are herein incorporated by reference):

Non patent literature 1. Takahashi, K. and Yamanaka, S., Cell, 126: 663-676 (2006)

Non patent literature 2. Okita, K. et al., Nature, 448: 313-317 (2007)

Non patent literature 3. Wernig, M. et al., Nature, 448: 318-324 (2007)

Non patent literature 4. Maherali, N. et al., Cell Stem Cell, 1: 55-70 (2007)

Non patent literature 5. Nakagawa, M. et al., Nat. Biotethnol., 26: 101-106 (2008)

Non patent literature 6. Takahashi, K. et al., Cell, 131: 861-872 (2007)

Non patent literature 7. Yu, J. et al., Science, 318: 1917-1920 (2007)

Non patent literature 8. Park, I. H. et al., Nature, 451: 141-146 (2008)

Patent literature 1. U.S. Publication No. 2009-0227032

Patent literature 2. International Publication No. WO2009/057831

SUMMARY OF THE INVENTION

An object of the present invention is to provide a novel method for improving iPS cell generation efficiency and factor for improving iPS cell generation efficiency.

It was reported that c-Myc has a transformation activity, while L-Myc has a very low transformation activity as compared with c-Myc (about 1 to 10% of c-Myc) (Birrer et al., Molecular and Cellular Biology 8: 2668-2673, 1988; and Barrett et al., Molecular and Cellular Biology 12: 3130-3137, 1992) (these documents are herein incorporated by reference).

The present inventors intensively investigated with respect to Myc variants having an effect to improve iPS cell generation efficiency, which is comparable to or greater than that of c-Myc. As a result, we have revealed that, by reducing the transformation activity of c-Myc (the activity to transform NIH3T3 cells), the activity to induce iPS cells increases as compared with c-Myc, and the percentage of the number of iPS cell colonies to the total number of colonies increases as well. We also have revealed that L-Myc and a variant thereof posses an increased activity to induce iPS cells as compared with native c-Myc and can increase the percentage of the number of iPS colonies to the total number of colonies, although L-Myc possesses only little transformation activity as described above.

As described above, the transformation activity of c-Myc acts rather negatively in the induction of human iPS cells. From the fact, it was shown that a Myc variant having a reduced transformation activity is useful in the induction of iPS cells.

There is a possibility that the transformation activity of c-Myc is involved in the tumor formation activity (Lutz, W. et al, Biochim Biophys Acta 1602: 61-71, 2002; Eilers, M. and Eisenman, RN Genes Dev 22: 2755-2766, 2008) (these documents are herein incorporated by reference) and therefore, it is expected that use of a Myc variant having a reduced transformation activity in the present invention for the induction of iPS cells leads to reduce the risk of tumor formation as compared with the case using c-Myc.

Thus, the present invention relates to the following subject matters.

[1] A method for improving iPS cell generation efficiency, which comprises a step of introducing a Myc variant having the following features (1) and (2):

(1) having an activity to improve iPS cell generation efficiency which is comparative to, or greater than that of c-Myc; and (2) having a transformation activity which is lower than that of c-Myc;

or a nucleic acid encoding said variant into somatic cells in a nuclear reprogramming step.

[2] The method according to [1], wherein the somatic cells are those derived from human.

[3] The method according to [1] or [2], wherein the activity of the Myc variant to transform NIH3T3 cells is lower than that of c-Myc.

[4] The method according to any one of [1] to [3], wherein the Myc variant is a c-Myc variant, an N-Myc variant or an L-Myc variant.

[5] The method according to [4], wherein the c-Myc variant has entire or partial deletion of amino acids at positions 1 to 41 in the amino acid sequence of human c-Myc as shown in SEQ ID NO:2.

[6] The method according to [5], wherein the c-Myc variant is any one of the following variants (1) to (4):

(1) a variant having deletion of amino acids at positions 1 to 41 in the amino acid sequence of human c-Myc as shown in SEQ ID NO:2, (2) a variant having deletion of amino acids at positions 1 to 64 in the amino acid sequence of human c-Myc as shown in SEQ ID NO:2, (3) a variant having deletion of amino acids at positions 1 to 107 in the amino acid sequence of human c-Myc as shown in SEQ ID NO:2, (4) a variant having deletion of amino acids at positions 1 to 13 and having a mutation at position 135 in the amino acid sequence of human c-Myc as shown in SEQ ID NO:2.

[7] The method according to [4], wherein the c-Myc variant has a mutation at position 135 in the amino acid sequence of human c-Myc as shown in SEQ ID NO:2.

[8] The method according to [6] or [7], wherein the mutation at position 135 in SEQ ID NO:2 is substitution or deletion of the amino acid.

[9] The method according to [8], wherein Trp at position 135 in SEQ ID NO:2 is substituted with Glu or Gly.

[10] The method according to [4], wherein the L-Myc variant has at least the amino acid sequence at and after position 70 in the amino acid sequence of human L-Myc as shown in SEQ ID NO:6.

[11] The method according to [10], wherein the L-Myc variant is either the following variant (1) or (2):

(1) a variant having at least amino acids at and after position 45 in the amino acid sequence of human L-Myc as shown in SEQ ID NO:6, (2) a variant having at least amino acids at and after position 22 in the amino acid sequence of human L-Myc as shown in SEQ ID NO:6.

[12] The method according to [4], wherein the L-Myc variant has a mutation at position 321 in the amino acid sequence of human L-Myc as shown in SEQ ID NO:6.

[13] The method according to [12], wherein the mutation at position 321 in SEQ ID NO:6 is substitution or deletion.

[14] The method according to [13], wherein Val at position 321 in SEQ ID NO:6 is substituted with Asp.

[15] A factor for improving generation efficiency of iPS cells, which comprises a Myc variant having the following features (1) and (2):

(1) having an activity to improve iPS cell generation efficiency which is comparative to, or greater than that of c-Myc; and (2) having a transformation activity which is lower than that of c-Myc;

or a nucleic acid encoding the variant.

[16] The factor according to [15], wherein the activity of the Myc variant to transform NIH3T3 cells is lower than that of c-Myc.

[17] The factor according to [15] or [16], wherein the Myc variant is a c-Myc variant, an N-Myc variant or an L-Myc variant.

[18] The factor according to [17], wherein the c-Myc variant has entire or partial deletion of amino acids at positions 1 to 41 in the amino acid sequence of human c-Myc as shown in SEQ ID NO:2.

[19] The factor according to [18], wherein the c-Myc variant is any one of the following variants (1) to (4):

(1) a variant having deletion of amino acids at positions 1 to 41 in the amino acid sequence of human c-Myc as shown in SEQ ID NO:2, (2) a variant having deletion of amino acids at positions 1 to 64 in the amino acid sequence of human c-Myc as shown in SEQ ID NO:2, (3) a variant having deletion of amino acids at positions 1 to 107 in the amino acid sequence of human c-Myc as shown in SEQ ID NO:2, (4) a variant having deletion of amino acids at positions 1 to 13 and having a mutation at position 135 in the amino acid sequence of human c-Myc as shown in SEQ ID NO:2.

[20] The factor according to [17], wherein the c-Myc variant has a mutation at position 135 in the amino acid sequence of human c-Myc as shown in SEQ ID NO:2.

[21] The factor according to [19] or [20], wherein the mutation at position 135 in SEQ ID NO:2 is substitution or deletion.

[22] The factor according to [21], wherein Trp at position 135 in SEQ ID NO:2 is substituted with Glu or Gly.

[23] The factor according to [17], wherein the L-Myc variant has at least the amino acid sequence at and after position 70 in the amino acid sequence of human L-Myc as shown in SEQ ID NO:6.

[24] The factor according to [23], wherein the L-Myc variant is either the following variant (1) or (2):

(1) a variant having at least amino acids at and after position 45 in the amino acid sequence of human L-Myc as shown in SEQ ID NO:6, (2) a variant having at least amino acids at and after position 22 in the amino acid sequence of human L-Myc as shown in SEQ ID NO:6.

[25] The factor according to [17], wherein the L-Myc variant has a mutation at position 321 in the amino acid sequence of human L-Myc as shown in SEQ ID NO:6.

[26] The factor according to [25], wherein the mutation at position 321 in SEQ ID NO:6 is substitution or deletion.

[27] The factor according to [26], wherein Val at position 321 in SEQ ID NO:6 is substituted with Asp.

[28] A method for preparing iPS cells, which comprises a step of introducing a Myc variant having the following features (1) and (2):

(1) having an activity to improve iPS cell generation efficiency which is comparative to, or greater than that of c-Myc; and (2) having a transformation activity which is lower than that of c-Myc;

or a nucleic acid encoding the variant, and a combination of one or more nuclear reprogramming factors into somatic cells.

[29] The method according to [28], wherein the somatic cells are those derived from human.

[30] The method according to [28] or [29], wherein the transformation activity is the activity to transform NIH3T3 cells.

[31] The method according to any one of [28] to [30], wherein the Myc variant is a c-Myc variant, an N-Myc variant or an L-Myc variant.

[32] The method according to [31], wherein the c-Myc variant has entire or partial deletion of amino acids at positions 1 to 41 in the amino acid sequence of human c-Myc as shown in SEQ ID NO:2.

[33] The method according to [32], wherein the c-Myc variant is any one of the following variants (1) to (4):

(1) a variant having deletion of amino acids at positions 1 to 41 in the amino acid sequence of human c-Myc as shown in SEQ ID NO:2, (2) a variant having deletion of amino acids at positions 1 to 64 in the amino acid sequence of human c-Myc as shown in SEQ ID NO:2, (3) a variant having deletion of amino acids at positions 1 to 107 in the amino acid sequence of human c-Myc as shown in SEQ ID NO:2, (4) a variant having deletion of amino acids at positions 1 to 13 and having a mutation at position 135 in the amino acid sequence of human c-Myc as shown in SEQ ID NO:2.

[34] The method according to [31], wherein the c-Myc variant has a mutation at position 135 in the amino acid sequence of human c-Myc as shown in SEQ ID NO:2.

[35] The method according to [33] or [34], wherein the mutation at position 135 in SEQ ID NO:2 is substitution or deletion.

[36] The method according to [35], wherein Trp at position 135 in SEQ ID NO:2 is substituted with Glu or Gly.

[37] The method according to [31], wherein the L-Myc variant has at least the amino acid sequence at and after position 70 in the amino acid sequence of human L-Myc as shown in SEQ ID NO:6.

[38] The method according to [37], wherein the L-Myc variant is either the following variant (1) or (2):

(1) a variant having at least amino acids at and after position 45 in the amino acid sequence of human L-Myc as shown in SEQ ID NO:6, (2) a variant having at least amino acids at and after position 22 in the amino acid sequence of human L-Myc as shown in SEQ ID NO:6.

[39] The method according to [31], wherein the L-Myc variant has a mutation at position 321 in the amino acid sequence of human L-Myc as shown in SEQ ID NO:6.

[40] The method according to [39], wherein the mutation at position 321 in SEQ ID NO:6 is substitution or deletion.

[41] The method according to [40], wherein Val at position 321 in SEQ ID NO:6 is substituted with Asp.

[42] The method according to any one of [28] to [41], wherein the combination of one or more nuclear reprogramming factors contains one or more factors selected from the group consisting of members of the Oct family, members of the Sox family, members of the Klf family, members of the Lin28 family and Nanog, as well as nucleic acids encoding them.

[43] The method according to [42], wherein the combination of nuclear reprogramming factors contains Oct3/4, Sox2 and Klf4, or nucleic acids encoding them.

[44] A kit for inducing iPS cells from somatic cells, which comprises an Myc variant having the following features (1) and (2):

(1) having an activity to improve iPS cell generation efficiency which is comparative to, or greater than that of c-Myc; and (2) having a transformation activity which is lower than that of c-Myc;

or a nucleic acid encoding the variant, and a combination of one or more nuclear reprogramming factors.

[45] The kit according to [44], wherein the somatic cells are those derived from human.

[46] The kit according to [44] or [45], wherein the transformation activity of the Myc variant which is an activity to transform NIH3T3 cells is lower than that of the c-Myc.

[47] The kit according to any one of [44] to [46], wherein the Myc variant is a c-Myc variant, an N-Myc variant or an L-Myc variant.

[48] The kit according to [47], wherein the c-Myc variant has entire or partial deletion of amino acids at positions 1 to 41 in the amino acid sequence of human c-Myc as shown in SEQ ID NO:2.

[49] The kit according to [48], wherein the c-Myc variant is any one of the following variants (1) to (4):

(1) a variant having deletion of amino acids at positions 1 to 41 in the amino acid sequence of human c-Myc as shown in SEQ ID NO:2, (2) a variant having deletion of amino acids at positions 1 to 64 in the amino acid sequence of human c-Myc as shown in SEQ ID NO:2, (3) a variant having deletion of amino acids at positions 1 to 107 in the amino acid sequence of human c-Myc as shown in SEQ ID NO:2, and (4) a variant having deletion of amino acids at positions 1 to 13 and having a mutation at position 135 in the amino acid sequence of human c-Myc as shown in SEQ ID NO:2.

[50] The kit according to [47], wherein the c-Myc variant has a mutation at position 135 in the amino acid sequence of human c-Myc as shown in SEQ ID NO:2.

[51] The kit according to [49] or [50], wherein the mutation at position 135 in SEQ ID NO:2 is substitution or deletion.

[52] The kit according to [51], wherein Trp at position 135 in SEQ ID NO:2 is substituted with Glu or Gly.

[53] The factor according to [47], wherein the L-Myc variant has at least the amino acid sequence at and after position 70 in the amino acid sequence of human L-Myc as shown in SEQ ID NO:6.

[54] The kit according to [53], wherein the L-Myc variant is either the following variant (1) or (2):

(1) a variant having at least amino acids at and after position 45 in the amino acid sequence of human L-Myc as shown in SEQ ID NO:6, (2) a variant having at least amino acids at and after position 22 in the amino acid sequence of human L-Myc as shown in SEQ ID NO:6.

[55] The kit according to [47], wherein the L-Myc variant has a mutation at position 321 in the amino acid sequence of human L-Myc as shown in SEQ ID NO:6.

[56] The kit according to [55], wherein the mutation at position 321 in SEQ ID NO:6 is substitution or deletion.

[57] The kit according to [56], wherein Val at position 321 in SEQ ID NO:6 is substituted with Asp.

[58] The kit according to any one of [44] to [57], wherein the combination of one or more nuclear reprogramming factors contains one or more factors selected from the group consisting of members of the Oct family, members of the Sox family, members of the Klf family, members of the Lin28 family and Nanog, as well as nucleic acids encoding them.

[59] The kit according to [58], wherein the combination of one or more nuclear reprogramming factors contains Oct3/4, Sox2 and Klf4, or nucleic acids encoding them.

[60] An iPS cell which comprises an exogenous nucleic acid encoding an Myc variant having the following features (1) and (2):

(1) having an activity to improve iPS cell generation efficiency which is comparative to, or greater than that of c-Myc; and (2) having a transformation activity which is lower than that of c-Myc.

[61] The iPS cell according to [60], wherein the exogenous nucleic acid encoding the Myc variant is integrated into the genome.

[62] A method for preparing somatic cells, which comprises carrying out a differentiation-inducing treatment on the iPS cells according to [60] or [61] to differentiate into the somatic cells.

[63] A method for preparing somatic cells, which comprises the following steps of:

(1) preparing iPS cells by the method according to any one of [28] to [43], and (2) carrying out a differentiation-inducing treatment on the iPS cells obtained in the above step (1) to differentiate into the somatic cells.

BRIEF DESCRIPTION OF THE DRAWINGS

FIG. 10 shows alignment of amino acid sequences of human c-Myc and N-Myc.

DETAILED DESCRIPTION OF THE INVENTION

Figure 1:
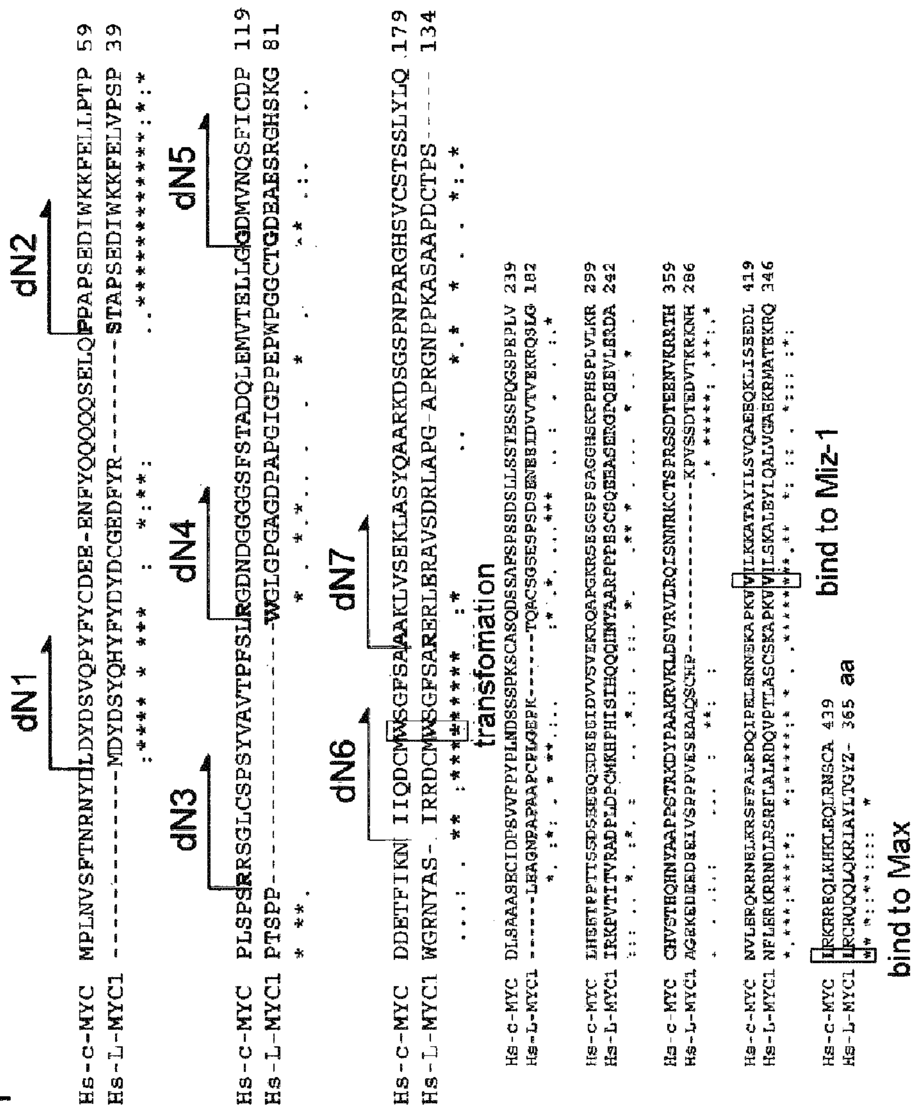
FIG. 1 shows alignment of amino acid sequences of human c-MYC and human L-MYC (L-MYC1). In the Figure, "dN1", "dN2", "dN3", "dN4", "dN5", "dN6", and "dN7" represent the N-terminal start site of each deletion mutant. Also, "transformation" represents the site involved in cell transformation in the c-Myc, "bind to Miz-1" represents the site involved in binding to Miz-1 protein in c-Myc, and "bind to Max" represents the site involved in binding to Max protein in c-Myc, respectively.

The present invention provides a method for improving iPS cell generation efficiency, which comprises a step of introducing an Myc variant having the features: (1) having an activity to improve iPS cell generation efficiency which is comparative to, or greater than that of c-Myc; and (2) having a transformation activity which is lower than that of c-Myc (hereinafter, the variant is referred to as "the Myc variant of the present invention"), or a nucleic acid encoding the variant into somatic cells in a nuclear reprogramming step. Since the nuclear reprogramming of somatic cells is carried out by introducing a combination of nuclear reprogramming factors into the somatic cells, the present invention also provides a method for preparing iPS cells, which comprises a step of introducing the Myc variant of the present invention or a nucleic acid encoding the variant and a combination of nuclear reprogramming factors into somatic cells. In the specification and claims, when the iPS cells can not be generated only by the the combination of nuclear reprogramming factors but can be generated by introducing the combination together with the Myc variant of the present invention or a nucleic acid encoding the variant into somatic cells, such generation is handled in the present invention as being included in "improvement of the generation efficiency".

(a) A Myc Variant of the Present Invention

The Myc variant of the present invention has the features of:

(1) having an activity to improve iPS cell generation efficiency which is comparative to, or greater than that of c-Myc; and (2) having a transformation activity which is lower than that of c-Myc.

In the specification and claims, "Myc variants" represents variants having a mutation in the amino acid sequence of c-Myc, N-Myc or L-Myc, and preferably variants having a mutation in the amino acid sequence of human c-Myc, N-Myc or L-Myc. The base sequence and the amino acid sequence of human c-Myc are shown in SEQ ID NO:1 and NO:2, the base sequence and the amino acid sequence of human N-Myc in SEQ ID NO:3 and NO:4, and the base sequence and the amino acid sequence of human L-Myc in SEQ ID NO:5 and NO:6, respectively.

In the above description, "mutation" means substitution, deletion and/or insertion of one or more amino acids in the original sequence. The number and positions of the substitution, deletion and insertion of amino acids in the Myc variants according to the present invention are not limited to particular ones, so far as the features of: (1) having an activity to improve iPS cell generation efficiency which is comparative to, or greater than that of c-Myc; and (2) having a transformation activity which is lower than that of c-Myc are retained.

For example, the Myc variant of the present invention can be prepared as a recombinant protein by a genetic recombination technology known per se using a nucleic acid encoding the Myc variant of the present invention obtained by carrying out desired mutation on a nucleic acid of c-Myc, N-Myc or L-Myc (in case of human, SEQ ID NO:1, NO:3 or NO:5), which is obtained from a cDNA derived from cells or tissues, for example, cells or tissues of thymus gland, bone marrow, spleen, brain, spinal card, heart, skeletal muscle, kidney, lung, liver, pancreas or prostate; precursor cells, stem cells or cancer cells of human or other mammals (for example, mouse, rat, monkey, pig, dog and the like) by cloning according to a conventional method.

In the above description, one can verify whether or not a variant has the feature (1), i.e. having an activity to improve iPS cell generation efficiency which is comparative to, or greater than that of c-Myc, by comparing the number of colonies of iPS cells generated when given combination of reprogramming factors (for example, three factors of Oct3/4, Sox2 and Klf4) and c-Myc are contacted with somatic cells, with the number of those colonies generated when the same combination of reprogramming factors and the Myc variant of the present invention instead of the c-Myc are contacted with somatic cells. Many papers have been published reporting the procedures to induce iPS cells. For example, the induction of mouse iPS cells can be carried out referring to Cell, 126: 663-676 (2006), and the induction of human iPS cells can be carried out referring to Cell, 131: 861-872 (2007).

In the above description, one can verify whether or not a variant has the feature (2), having a transformation activity which is lower than that of c-Myc, by comparing the degree of somatic cells transformed when c-Myc is contacted with somatic cells, with the degree of those transformed when the Myc variant of the present invention instead of the c-Myc is contacted with somatic cells. For example, mouse NIH3T3 cells can be used as the somatic cells. The degree of transformation can be evaluated by observing cell morphology under a microscope.

Specifically, a c-Myc variant of the present invention may be a c-Myc variant which has entire or partial deletion of amino acids at positions 1 to 41 in the amino acid sequence of human c-Myc as shown in SEQ ID NO:2, for example. The variant having "partial" deletion (at positions 1 to 41) is not limited to particular ones, so far as the c-Myc variant has the partial deletion retain the features: (1) having an activity to improve iPS cell generation efficiency which is comparative to, or greater than that of c-Myc; and (2) having a transformation activity which is lower than that of c-Myc. For example, variants having deletion of amino acids at positions 1 to 13, positions 1 to 15, positions 1 to 20, positions 1 to 25, positions 1 to 30, positions 1 to 35, or positions 1 to 40 in SEQ ID NO:2 are exemplified.

Also, a Myc variant having "entire" deletion at positions 1 to 41 is not limited to particular ones, so far as the above features (1) and (2) are retained, but it is desirable that it does not have deletion at and after position 125, preferably at and after position 120 in SEQ ID NO:2.

More specifically, the following c-Myc variants (1) to (4) are mentioned, for example:

(1) a variant having deletion of amino acids at positions 1 to 41 in the amino acid sequence of human c-Myc as shown in SEQ ID NO:2,
(2) a variant having deletion of amino acids at positions 1 to 64 in the amino acid sequence of human c-Myc as shown in SEQ ID NO:2,
(3) a variant having deletion of amino acids at positions 1 to 107 in the amino acid sequence of human c-Myc as shown in SEQ ID NO:2,
(4) a variant having deletion of amino acids at positions 1 to 13 and having a mutation at position 135 in the amino acid sequence of human c-Myc as shown in SEQ ID NO:2.

In this connection, position 135 in SEQ ID NO:2 (position 136 in mouse c-Myc) is located in the region essential for interaction between c-Myc and a nucleic acid factor which plays an important role in transformation activity of the c-Myc (Brough et al., Molecular and Cellular Biology 15 (3): 1536-1544, 1995, this document is herein incorporated by reference). The mutation at position 135 may include substitution or deletion. Specifically, the substitution may include substitution of Trp at position 135 (position 136 in mouse c-Myc) with Glu or Gly, see the above Brough et al., and the deletion includes deletion of amino acids at positions 128 to 144 (deletion of amino acids at positions 129 to 145 in mouse), see the above Brough et al.

N-Myc has a transformation activity comparative to that of c-Myc, and can functionally be substituted for the c-Myc [Genes & Dev. 14 (11): 1390-1399 (2000)] (this document is herein incorporated herein by reference). Also, the amino acid at position 135 of N-Myc is identical with that of c-Myc (see the alignment of FIG. 10). Accordingly, a N-Myc variant corresponding to the above c-Myc variant of the present invention, i.e. N-Myc variants having a mutation at corresponding positions according to the alignment with the c-Myc, are also included in the scope of the Myc variants of the present invention.

Examples of L-Myc variants of the present invention include L-Myc variants having at least amino acids at and after position 70 in the amino acid sequence of human L-Myc as shown in SEQ ID NO:6. The L-Myc variant is not limited to particular ones, so far as it retains the features: (1) having an activity to improve iPS cell generation efficiency which is comparative to, or greater than that of c-Myc; and (2) having a transformation activity which is lower than that of c-Myc. Specifically, the following L-Myc variant (1) or (2) may preferably be employed:

(1) a variant having at least amino acids at and after position 45 in the amino acid sequence of human L-Myc as shown in SEQ ID NO:6,
(2) a variant having at least amino acids at and after position 22 in the amino acid sequence of human L-Myc as shown in SEQ ID NO:6.

Variants obtained by introducing further mutation, for example, substitution, deletion and/or insertion of one to several amino acids, to the above-described Myc variant of the present invention are also included in the scope of the "Myc variant of the present invention", if it retains the features: (1) having an activity to improve iPS cell generation efficiency which is comparative to, or greater than that of c-Myc; and (2) having a transformation activity which is lower than that of c-Myc.

Introduction of a Myc variant protein of the present invention into somatic cells can be carried out using a method known per se for introducing a protein into cells. Such a method includes, for example, a method using a protein transduction reagent, a method using a protein transduction domain (PTD) or cell-permeable peptide (CPP) fusion protein, a microinjection method, etc. As a protein transduction reagent, BioPOTER Protein Delivery Reagent (Gene Therapy Systems), Pro-Ject™ Protein Transfection Reagent (PIERCE) and ProVectin (IMGENEX) based on a cationic lipid, Profect-1 (Targeting Systems) based on a lipid, Penetrain Peptide (Q biogene) and Chariot Kit (Active Motif) based on a membrane-permeable peptide, GenomONE (Ishihara Sangyo Kaisha, Ltd.) utilizing an HVJ envelope (inactivated Sendai virus) and the like are marketed. The introduction can be carried out according to the protocol attached to these reagents, and the general procedures are as follows. The protein factor for improving the generation efficiency of the present invention is diluted in a suitable solvent such as PBS or HEPES, a transduction reagent is added to the solution, and the mixture is incubated at room temperature for about 5-15 minutes to form a complex. The complex is added to cells in a serum-free medium and incubated at 37° C. for one to several hours. Thereafter, the medium is removed to replace it with a serum-containing medium.

As PTDs, those developed by using a cell membrane-spanning domain of a protein such as AntP derived from drosophila, TAT derived from HIV [Frankel, A. et al, Cell 55, 1189-93 (1988); Green, M. & Loewenstein, P. M., Cell 55, 1179-88 (1988)], Penetratin [Derossi, D. et al, J. Biol. Chem. 269, 10444-50 (1994)], Buforin II [Park, C. B. et al., Proc. Natl. Acad. Sci. USA 97, 8245-50 (2000)], Transportan [Pooga, M. et al., FASEB J. 12, 67-77 (1998)], MAP (model amphipathic peptide) [Oehlke, J. et al., Biochim. Biophys. Acta. 1414, 127-39 (1998)], K-FGF [Lin, Y. Z. et al., J. Biol. Chem. 270, 14255-14258 (1995)], Ku70 [Sawada, M. et al., Nature Cell Biol. 5, 352-7 (2003)], Prion [Lundberg, P. et al., Biochem. Biophys. Res. Commun. 299, 85-90 (2002)], pVEC [Elmquist, A. et al., Exp. Cell Res. 269, 237-44 (2001)], Pep-1 [Morris, M. C. et al., Nature Biotechnol. 19, 1173-6 (2001)], Pep-7 [Gao, C. et al., Bioorg. Med. Chem. 10, 4057-65 (2002)], SynBl [Rousselle, C. et al., MoI. Pharmacol. 57, 679-86 (2000)], HN-I [Hong, F. D. & Clayman, G L., Cancer Res. 60, 6551-6 (2000)] and VP22 derived from HSV and the like can be used. The CPP derived from PTD includes polyarginines such as 11R [Cell Stem Cell, 4: 381-384 (2009)] and 9R [Cell Stem Cell, 4: 472-476 (2009)]. (All the documents mentioned in this paragraph are herein incorporated by reference.)

A vector integrating the cDNA of the Myc variant of the present invention and the PTD or CPP sequence for expressing the fusion protein may be prepared and the fusion protein may be recombinantly expressed. The fusion protein is then recovered and used for transduction. The transduction can be carried out in a manner similar to that described above, except that no protein transduction reagent is added.

Microinjection is a method in which a protein solution is charged into a glass needle having a tip diameter of about 1 μm and puncture-introduced into cells. The microinjection can reliably introduce the protein into cells.

Alternatively, other methods for introducing a protein into cells such as an electroporation method, a semi-intact cell method [Kano, F. et al., Methods in Molecular Biology, Vol. 322, 357-365 (2006)], and an introducing method with a Wr-t peptide [Kondo, E. et al., Mol. Cancer Ther. 3 (12), 1623-1630 (2004)] may be used. (All the documents mentioned in this paragraph are herein incorporated by reference.)

Procedures for introducing the protein may be carried out one or more times, for example, 1 to 10 times or 1 to 5 times arbitrarily. Preferably, the procedures may be carried out two or more times, for example, 3 or 4 times repeatedly. When the procedures are carried out repeatedly, the interval may be, for example, 6 to 48 hours, and preferably 12 to 24 hours.

The nucleic acid encoding the Myc variant of the present invention is not limited to particular ones, so far as it encodes the above Myc variant protein of the present invention. The nucleic acid may be DNA or RNA, or DNA/RNA chimera. DNA is preferably used. Also, the nucleic acid may be double-stranded or single-stranded. In the case of double-stranded nucleic acid is used, it may be double-stranded DNA, double-stranded RNA or DNA:RNA hybrid.

For example, the nucleic acid encoding the Myc variant of the present invention can be obtained by introducing the desired mutation on a nucleic acid of c-Myc, N-Myc or L-Myc (in case of human, SEQ ID NO:1, NO:3 or NO:5), which is obtained from a cDNA derived from cells or tissues [for example, cells or tissues of thymus gland, bone marrow, spleen, brain, spinal card, heart, skeletal muscle, kidney, lung, liver, pancreas or prostate; precursor cells, stem cells or cancer cells of the cells; and the like] of human or other mammals (for example, mouse, rat, monkey, pig, dog and the like) by cloning according to a conventional method.

Introduction of the nucleic acid encoding the Myc variant of the present invention into somatic cells can be carried out using a method known per se for introducing a gene into cells. The nucleic acid encoding the Myc variant of the present invention may be integrated into a suitable expression vector containing a promoter which can function in the host (somatic cells) in the manner the nucleic acid is operably linked to the promoter. For example, viral vectors such as retrovirus, lentivirus, adenovirus, adeno-associated virus, herpesvirus, and Sendai virus, as well as animal cell expression plasmids (for example, pA1-11, pXT1, pRc/CMV, pRc/RSV, and pcDNAI/Neo) and the like can be used as an expression vector.

The types of vectors used can be selected suitably depending on the intended use of the obtained iPS cells. For example, it is possible to use an adenoviral vector, a plasmid vector, an adeno-associated virus vector, a retroviral vector, a lentiviral vector, a Sendai virus vector and the like.

Promoters used in the expression vector may be, for example, an EF1α promoter, a CAG promoter, an SRα promoter, an SV40 promoter, an LTR promoter, a CMV (cytomegalovirus) promoter, an RSV (Rous sarcoma virus) promoter, an MoMuLV (Moloney murine leukemia virus) LTR, HSV-TK (herpes simplex virus thymidine kinase) promoter and the like. Among them, an EF1α promoter, a CAG promoter, an MoMuLV LTR, CMV promoter, an SRα promoter and the like are preferably used.

In addition to the promoter, the expression vectors may optionally contain an enhancer, a poly-A additional signal, a selection marker gene, an SV40 replication origin and the like. Examples of the selection marker gene include a dihydrofolate reductase gene, a neomycin-resistant gene and a puromycin-resistant gene.

The nucleic acid encoding the Myc variant of the present invention may be integrated alone into the expression vector, or integrated into one expression vector together with one or more genes of reprogramming factors. It may be preferable to select the former integration when a retroviral or lentiviral vector having a high gene transduction efficiency is used, and it may be preferable to select the latter integration when a plasmid, adenovirus or episomal vector or a similar vector is used. However, there is no particular limitation in the selection.

In the above description, when the nucleic acid encoding the Myc variant of the present invention as well as one or more reprogramming genes are integrated into one expression vector, these multiple genes may be integrated into the expression vector, preferably via a sequence which enables polycistronic expression. By the use of the sequence which enables polycistronic expression, it becomes possible to express multiple genes integrated into one expression vector efficiently. The sequences enabling polycistronic expression include, for example, a 2A sequence of foot-and-mouth disease virus (SEQ ID NO:7; PLoS ONE3, e2532, 2008, Stem Cells 25, 1707, 2007) and an IRES sequence (U.S. Pat. No. 4,937,190), and preferably a 2A sequence is used (these documents are herein incorporated by reference).

The expression vector containing the nucleic acid encoding the Myc variant of the present invention can be introduced into cells by a technique known per se depending on the type of the vector. A viral vector can be prepared, for example, by introducing a plasmid containing the above nucleic acid into a suitable packaging cell (e.g., Plat-E cells) or complementing cell line (e.g., 293 cells), and culturing the cells. The viral vector produced in the culture supernatant is recovered, and the somatic cells are infected with the vector by a suitable method depending on the vector. For example, infection procedures using a retroviral vector is disclosed in WO2007/69666, *Cell,* 126, 663-676 (2006) and *Cell,* 131, 861-872 (2007), and those using a lentiviral vector are disclosed in *Science,* 318, 1917-1920 (2007). If iPS cells are used for regeneration therapy, expression or reactivation of the Myc variant of the present invention or activation of endogenous gene present near the position into which the exogenous nucleic acid of the variant is integrated may increase the risk of tumor formation in the tissues regenerated from the differentiated cells derived from the iPS cells. Accordingly, it is preferable that the nucleic acid encoding the Myc variant of the present invention is not integrated into the chromosome of the cells but is transiently expressed in the cells. From this viewpoint, it is preferable to use an adenoviral vector which is rarely integrated into the chromosome. Procedures using the adenoviral vector are described in *Science,* 322, 945-949 (2008). Adeno-associated viral vectors are also preferable since they have a low frequency of integration into the chromosome and a low cytotoxicity and a low inflammation-evoking activity as compared with adenoviral vectors. Sendai virus vectors are also preferable since they can be present extrachromosomally in a stable manner and can be decomposed by siRNA and removed if needed. Sendai virus vectors described in *J. Biol. Chem.,* 282, 27383-27391 (2007), *Proc. Jpn. Acad., Ser. B* 85, 348-362 (2009), or JP Patent No. 3,602,058(All the documents mentioned in this paragraph are herein incorporated by reference.) may be used in the present invention.

When a retroviral vector or a lentiviral vector is used, silencing of the introduced gene may occur temporarily and then, the gene may be reactivated later. Accordingly, a method can be used preferably in which the nucleic acid encoding the Myc variant of the present invention is excised, for example, using a Cre/loxP system when it becomes unnecessary. Thus, loxP sequences are located at both ends of the above nucleic acid, a Cre recombinase is allowed to act on the cells using a plasmid or adenoviral vector after induction of iPS cells so that the region flanked with the loxP sequences is excised. Also, an enhancer-promoter sequence in an LTR U3 region has a possibility of controlling upward adjacent host genes by insertion mutation. Accordingly, it is more preferable to use 3'-self-inactivating (SIN) LTR in which the above sequence is deleted or substituted with a polyadenylation sequence of SV40 and the like to avoid an expression control of endogenous genes by the LTR outside of the loxP sequence which remains in a genome without being excised. Concrete measures using the Cre-loxP system and the SIN LTR are disclosed in Soldner et al., *Cell,* 136: 964-977 (2009), Chang et al., *Stem Cells,* 27: 1042-1049 (2009) and others. (All the documents mentioned in this paragraph are herein incorporated by reference.)

On the other hand, when a plasmid vector which is a non-viral vector is used, it is possible to introduce the vector into the cells using a method such as a lipofection method, a liposome method, an electroporation method, a calcium phosphate coprecipitation method, a DEAE dextran method, a microinjection method, and a gene gun method. Procedures using plasmid as a vector are described, for example, in *Science,* 322, 949-953 (2008) (this document is herein incorporated by reference).

In the case of a plasmid or adenoviral vector is used, the gene introduction may be carried out one or more times, for example, 1 to 10 times or 1 to 5 times arbitrarily. When two or more expression vectors are introduced into the somatic cells, it is preferable to introduce all types of these expression vectors concomitantly into the somatic cells. Even in this case, the introduction procedures may be carried out one or more times, for example, 1 to 10 times or 1 to 5 times arbitrarily. Preferably, the procedures may be carried out two or more times, for example, 3 times or 4 times repeatedly.

Even when an adenoviral or plasmid vector is used, a gene introduced may be integrated into the chromosome. Accordingly, it is eventually necessary to verify the absence of a gene insertion into the chromosome by southern blotting or PCR. For this purpose, it may be convenient to use a means in which a gene to be introduced is integrated into the chromosome and the gene is then removed, as in the above Cre-loxP system. In another preferred embodiment, a gene is integrated into the chromosome using a transposon, a transferase is then allowed to act on the cells using a plasmid or adenoviral vector so that the integrated gene is entirely removed from the chromosome. Preferred transposons include, for example, piggyBac which is a transposon derived from lepidopterous insects. Procedures using the piggyBac transposon are disclosed in Kaji, K. et al., *Nature,* 458: 771-775 (2009), and Woltjen et al., *Nature,* 458: 766-770 (2009). (Those documents are herein incorporated by reference.)

Another preferred non-integral vector includes an episomal vector which is autonomously replicable in extrachromosome. Procedures using the episomal vector are disclosed in Yu et al., *Science,* 324, 797-801 (2009) (this document is herein incorporated by reference). If needed, it is also possible to construct an expression vector in which the nucleic acid encoding the Myc variant of the present invention is inserted into an episomal vector having loxP sequences located in the same direction at 5' and 3' of a vector element necessary for replication of the episomal vector, and to introduce the expression vector into the somatic cells.

Examples of the episomal vectors include a vector containing as a vector element a sequence necessary for autonomous replication derived from EBV, SV40 or the like. Specifically, the vector element necessary for autonomous replication is a replication origin and a gene encoding the protein which binds to the replication origin to control the replication, for example, replication origin oriP and EBNA-1 gene in EBV, and replication origin on and SV40 large T antigen gene in SV40.

The episomal expression vector contains a promoter which controls transcription of the nucleic acid encoding the Myc variant of the present invention that is operably linked to the promoter. As a promoter, the above described promoters may be used. If needed, the episomal expression vector may further contain an enhancer, a poly-A additional signal, a selection marker gene and the like, as described above. The selection marker gene includes, for example, a dihydrofolate reductase gene, a neomycin-resistant gene and the like.

Examples of the loxP sequences used in the present invention include a wild-type loxP sequence derived from bacteriophage P1 (SEQ ID NO:8) as well as any mutated loxP sequences which can delete the sequence between the loxP sequences by undergoing recombination when they are located in the same direction at both positions sandwiching the vector element necessary for replication of the introduced gene. Examples of mutated loxP sequences include lox71 (SEQ ID NO:9) having a mutation in the 5' repeat sequence, lox66 (SEQ ID NO:10) having a mutation in the 3' repeat sequence, lox2272 or lox511 having a mutation in the spacer portion. Two loxP sequences located at 5' and 3' of the vector element may be the same or different. However, when mutated loxP sequences having a mutation in the spacer portion are used, the same sequences are used (e.g., two lox2272s or two lox511s). Preferably, a combination of a mutated loxP sequence having a mutation in the 5' repeat sequence (e.g., lox71) and a mutated loxP sequence having a mutation in the 3' repeat sequence (e.g., lox66) may be used used. In this case, the loxP sequences remaining on the chromosome as a result of the recombination have double mutation in the 5' and 3' repeat sequences, and therefore, they are hardly recognized by a Cre recombinase and a risk of causing deletion mutation of the chromosome by an unnecessary recombination is reduced. When lox71 and lox66 are used, any of these mutated loxP sequences may be located at any of the 5' and 3' of the above vector element. However, the mutated loxP sequences are needed to be inserted in a direction in which the mutation site is located at outer ends of the loxP sequences.

Two loxP sequences are located in the same direction at 5' and 3' of the vector element necessary for replication of the introduced gene (i.e., a replication origin, or a gene sequence encoding a protein which binds to the replication origin to control the replication). The vector element sandwiched by the loxP sequences may be any one or both of a replication origin and a gene sequence encoding a protein which binds to the replication origin to control the replication.

The episomal vector can be introduced into cells using, for example, a lipofection method, a liposome method, an electroporation method, a calcium phosphate coprecipitation method, a DEAE dextran method, a microinjection method, a gene gun method and others. Specifically, it is possible to use a method described, for example, in *Science,* 324: 797-801 (2009).

The verification of removal of the vector element necessary for replication of the introduced gene from the iPS cells can be carried out by using a nucleic acid containing a base sequence inside of the vector element and/or adjacent to the loxP sequences as a probe or a primer, conducting a southern blotting analysis or a PCR analysis with the episomal fraction isolated from the iPS cells as a template, and evaluating the presence or absence of the bands or evaluating the length of the detected bands. The episomal fraction may be prepared by a method well known in the art. For example, a method described in *Science,* 324: 797-801 (2009) may be used.

(b) Source of the Somatic Cells

The somatic cells which can be used as starting material for preparing iPS cells in the present invention may be any cells derived from a mammal except for germ cells. The mammal may be, for example, human, mouse, monkey, cattle, pig, rat or dog. Somatic cells derived from human are particularly preferred. Specifically, the following cells are exemplified: keratinizing epithelial cells (e.g., keratinizing epidermal cells), mucosal epithelial cells (e.g., epithelial cells of tongue surface), exocrine epithelial cells (e.g., mammary gland cells), hormone-secreting cells (e.g., adrenal medullary cells), metabolism and storage cells (e.g., hepatic cells), luminal epithelial cells constituting an interface (e.g., alveolar type I cells), luminal epithelial cells of an inner chain tube (e.g., vascular endothelial cells), cells having villi with a transporting capacity (e.g., respiratory tract epithelial cells), cells for extracellular matrix secretion (e.g., fibroblasts), contractile cells (e.g., smooth muscle cells), cells of blood and immune system (e.g., T-lymphocytes), cells involved in sensation (e.g., rod cells), neurons of autonomic nervous system (e.g., cholinergic neurons), supporting cells of a sensory organ and peripheral neurons (e.g., associated cells), nerve cells and glia cells of central nervous system (e.g., astrocytes), pigment cells (e.g., retinal pigment epithelial cells), and precursor cells of the above cells (tissue precursor cells) and others. The degree of the cell differentiation and the age of the animal from which the somatic cells are obtained are not limited to particular ones, and undifferentiated precursor cells (including somatic stem cells) and ultimately differentiated mature cells can be used evenly as an origin of the somatic cells in the present invention. The undifferentiated precursor cells include, for example, tissue stem cells (somatic stem cells) such as neural stem cells, hematopoietic stem cells, mesenchymal stem cells, and pulpal stem cells.

Individuals of mammals which serve as a source for obtaining the somatic cells are not limited to particular ones. When the obtained iPS cells are used in regeneration therapy practiced on a human patient, it is particularly preferable to obtain the patient's own somatic cells or somatic cells of a person having an HLA type that is identical or substantially identical to that of the patient from the viewpoint of preventing the rejection reaction. The "substantially identical" HLA type means that, the HLA type is coincident to the extent that the cells obtained by differentiating the iPS cells can be engrafted when the cells are transplanted into the patient with the use of an immune suppressor. For example, this is the case when there is a coincidence of main HLAs (for example, three loci of HLA-A, HLA-B and HLA-DR) (the same applies to the following). On the other hand, when the iPS cells are not administered or transplanted to a human, for example, when they are used for evaluating a patient's drug susceptibility or the presence or absence of side effects, it is also desirable to obtain the patient's own somatic cells or somatic cells of a person having an identical gene polymorphism correlating with the drug susceptibility or side effect.

The somatic cells separated from a mammal can be precultured, before being subjected to a nuclear reprogramming step, in a medium known per se suitable for cultivation depending on the type of the cells. Non limited examples of media to be used in this connection include a minimum essential medium (MEM) containing a fetal bovine serum of about 5 to 20%, a Dulbecco's modified Eagle's medium (DMEM), an RPMI1640 medium, a 199 medium and an F12 medium. If a transduction reagent such as, for example, a cationic liposome is used when contacting somatic cells with the Myc variant of the present invention and the combination of nuclear reprogramming factors (also if needed, an additional factor for improving iPS cell generation efficiency as described below), it may be preferable to replace the medium with a serum-free medium in order to prevent the reduction of the transduction efficiency.

(c) Nuclear Reprogramming Factor

In the present invention, the "combination of nuclear reprogramming factors" is a combination of one or more factors which can induce iPS cells from somatic cells by introducing the same into the somatic cells, or introducing the same into the somatic cells together with the Myc variant of the present invention or a nucleic acid encoding the Myc variant, and may be any factors such as a protein or a nucleic acid encoding the protein factor (including a vector in which the nucleic acid is integrated), or a low molecular compound. Examples of preferable combinations of nuclear reprogramming factors that are combinations of protein factors or nucleic acids encoding the protein factors may include followings. Although the names of the protein factors are disclosed in the following list, nucleic acids encoding the protein factors may also be used preferably. The documents mentioned in the following list are herein incorporated by reference.

(1) Oct3/4, Klf4, c-Myc;

(2) Oct3/4, Klf4, c-Myc, Sox2 [wherein Sox2 can be replaced with Sox1, Sox3, Sox15, Sox17 or Sox18, Klf4 with Klf1, Klf2 or Klf5, and c-Myc with T58A (activated mutant), N-Myc or L-Myc];

(3) Oct3/4, Klf4, c-Myc, Sox2, Fbx15, Nanog, Eras, ECAT15-2, TclI, β-catenin (activated mutant S33Y);

(4) Oct3/4, Klf4, c-Myc, Sox2, TERT, SV40 Large T antigen (hereinafter, SV40LT);

(5) Oct3/4, Klf4, c-Myc, Sox2, TERT, HPV16 E6;

(6) Oct3/4, Klf4, c-Myc, Sox2, TERT, HPV16 E7;

(7) Oct3/4, Klf4, c-Myc, Sox2, TERT, HPV6 E6, HPV16 E7;

(8) Oct3/4, Klf4, c-Myc, Sox2, TERT, Bmil;

[For the above combinations, see WO 2007/069666. For the replacement of Sox2 with Sox18, and the replacement of Klf4 with Klf1 or Klf5 in the above combination (2), see *Nature Biotechnology,* 26, 101-106 (2008)). For the combination "Oct3/4, Klf4, c-Myc, Sox2", also see *Cell,* 126, 663-676 (2006), Cell, 131, 861-872 (2007) and others. Regarding the combination "Oct3/4, Klf2 (or Klf5), c-Myc, Sox2", also see *Nat. Cell Biol.,* 11, 197-203 (2009). Regarding the combination "Oct3/4, Klf4, c-Myc, Sox2, hTERT, SV40LT", also see *Nature,* 451, 141-146 (2008).];

(9) Oct3/4, Klf4, Sox2 [see *Nature Biotechnology,* 26, 101-106 (2008)];

(10) Oct3/4, Sox2, Nanog, Lin28 [see *Science,* 318, 1917-1920 (2007)];

(11) Oct3/4, Sox2, Nanog, Lin28, hTERT, SV40LT [see *Stem Cells,* 26, 1998-2005 (2008)];

(12) Oct3/4, Klf4, c-Myc, Sox2, Nanog, Lin28 [see *Cell Research* (2008) 600-603];

(13) Oct3/4, Klf4, c-Myc, Sox2, SV40LT [see *Stem Cells,* 26, 1998-2005 (2008)];

(14) Oct3/4, Klf4 [see *Nature* 454: 646-650 (2008), Cell Stem Cell, 2: 525-528 (2008)];

(15) Oct3/4, c-Myc [see *Nature* 454: 646-650 (2008)];

(16) Oct3/4, Sox2 [see Nature, 451, 141-146 (2008), WO2008/118820];

(17) Oct3/4, Sox2, Nanog [see WO2008/118820];

(18) Oct3/4, Sox2, Lin28 [see WO2008/118820];

(19) Oct3/4, Sox2, c-Myc, Esrrb [wherein the Essrrb can be replaced with Esrrg; see *Nat. Cell Biol.,* 11, 197-203 (2009)];

(20) Oct3/4, Sox2, Esrrb [see *Nat. Cell Biol.,* 11, 197-203 (2009)];

(21) Oct3/4, Klf4, L-Myc;

(22) Oct3/4, Nanog;

(23) Oct3/4 [*Cell* 136: 411-419 (2009), *Nature,* 08436, doi: 10.1038 published online (2009)];

(24) Oct3/4, Klf4, c-Myc, Sox2, Nanog, Lin28, SV40LT [see *Science,* 324: 797-801 (2009)].

In the above combinations (1) to (24), Oct3/4 can be replaced with the other member of the Oct family such as Oct1A and Oct6. Also, Sox2 (or Sox1, Sox3, Sox15, Sox17, Sox18) can be replaced with the other member of the Sox family such as Sox7.

When wild-type c-Myc or N-Myc is contained in the above combinations (1) to (24), a combination which contains the listed factors except for wild-type c-Myc or N-Myc is preferably used as the combination of nuclear reprogramming factors used in combination with the Myc variant of the present invention. When a member of the Myc family other than c-Myc or N-Myc is contained in the above combinations (1) to (24), the combination of nuclear reprogramming factors may or may not contain the member of the Myc family. Preferably, remaining factors excepting the members of the Myc family are used as the combination of nuclear reprogramming factors to be used together with the Myc variant of the present invention. When a member of the Myc family is not contained in the above combinations (1) to (24), the combination of factors may be used as the combination of nuclear reprogramming factors together with the Myc variant of the present invention.

A combination containing any additional factor in addition to the above disclosed nuclear reprogramming factors is also suitably used as the "combination of nuclear reprogramming factors" to be used in combination of the Myc variant of the present invention. Under a condition in which the somatic cells subjected to nuclear reprogramming inherently express a part of any of the above combinations (1) to (24) in a sufficient level for the nuclear reprogramming, a combination which contains only the remaining factors excepting the factor inherently expressed in the cells is also suitably used as the "combination of nuclear reprogramming factors" to be used in combination with the Myc variant of the present invention.

Among the above combinations, a combination of one or more factors selected from members of the Oct family, the Sox family, the Klf family and the Lin28 family and Nanog is exemplified as preferred combination of nuclear reprogramming factors.

Among others, a combination of three factors of Oct3/4, Sox2 and Klf4 [i.e., the combination of above (9)] is preferred when the iPS cells obtained are used for therapeutic purposes.

The information relating to mouse and human cDNA sequences of the above proteinic factors can be obtained by referring the NCBI accession numbers described in WO 2007/069666 (in this reference, Nanog is mentioned in the name of "ECAT4"). The information relating to mouse and human cDNA sequences of Lin28, Lin28B, Esrrb, Esrrg, and L-Myc can be obtained by referring the following NCBI accession numbers, respectively. Those skilled in the art can easily isolate these cDNAs.

| Name of gene | Mouse | Human |
|---|---|---|
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| L-Myc | NM_008506 | NM_001033081 |

When a protein factor itself is used as a nuclear reprogramming factor, the factor can be prepared by inserting the isolated cDNA into a suitable expression vector, introducing the resulting vector into host cells, culturing the cells and recovering the recombinant protein factor from the culture. On the other hand, when a nucleic acid encoding the protein factor is used as a nuclear reprogramming factor, a cDNA obtained is inserted into a viral vector, an episomal vector or a plasmid vector to construct an expression vector, in a manner similar to that of the case of a nucleic acid encoding the above described c-Myc variant of the present invention, and the resulting expression vector is provided to the nuclear reprogramming step. If needed, it is possible to utilize the above described Cre-loxP system or piggyBac transposon system. Also, when two or more nucleic acids encoding the protein factors are introduced into the cells as nuclear reprogramming factors, these nucleic acids may be carried on separate vectors, or joined in tandem to constitute a polycistronic vector. In the latter case, it is desirable to join a 2A self-cleaving peptide of foot-and-mouth disease virus between the nucleic acids in order to enable an efficient polycistronic expression (see *Science,* 322, 949-953, 2008 and others) (this document is herein incorporated by reference).

The contact of a nuclear reprogramming factor with somatic cells can be carried out as follows: (a) when the nuclear reprogramming factor is a protein factor, the contact may be carried out in a manner similar to that of the case of the Myc variant of the present invention as described above, (b) when the nuclear reprogramming factor is a nucleic acid encoding the protein factor of the above (a), the contact may be carried out in a manner similar to that of the case of a nucleic acid encoding the Myc variant of the present invention as described above, and (c) when the nuclear reprogramming factor is a low molecular compound, the contact may be carried out by dissolving the compound in an aqueous or non-aqueous medium in a suitable concentration, adding the solution of the compound to a medium [for example, a minimum essential medium (MEM) containing a fetal bovine serum of about 5 to 20%, a Dulbecco's modified Eagle's medium (DMEM), an RPMI1640 medium, a 199 medium, an F12 medium and the like] suitable for cultivation of the somatic cells isolated from human or other mammals so that the concentration of the compound is in a range which is sufficient for nuclear reprogramming and does not cause cytotoxicity, and culturing the somatic cells in the medium for a certain period of time. The concentration of the compound used as a nuclear reprogramming factor varies depending on the type of the compound, and is suitably selected in a range of about 0.1 nM to about 100 nM. The contact time is not limited to a particular one when the time is sufficient for achieving the nuclear reprogramming of cells. Usually, the compound and cells may be retained in a medium until positive colonies appear.

(d) Other Factors for Improving iPS Cell Generation Efficiency

The generation efficiency of iPS cells was low in previously reported procedures and a variety of factors for improving the efficiency have been proposed. Thus, it can be expected that iPS cell generation efficiency is further increased by contacting a factor for improving iPS cell generation efficiency with the somatic cells in addition to the above Myc variant according to the present invention.

Examples of factors for improving iPS cell generation efficiency other than Myc variant of the present invention include, for example, the following factors: histone deacetylase (HDAC) inhibitors [for example, low molecular inhibitors such as valproic acid (VPA) (Nat. Biotechnol., 26(7): 795-797 (2008)), Trichostatin A, sodium butylate, MC 1293, and M344, nucleic acid expression inhibitors such as siRNA and shRNA against HDAC (e.g., HDAC1 siRNA Smartpool® (Millipore), HuSH 29mer shRNA Constructs against HDAC1 (OriGene) and others), etc.], DNA methyl transferase inhibitors (for example, 5'-azacytidine) (Nat. Biotechnol., 26(7): 795-797 (2008)), G9a histone methyl transferase inhibitors [for example, low molecular inhibitors such as BIX-01294 (Cell Stem Cell, 2: 525-528 (2008)), nucleic acid expression inhibitors such as siRNA and shRNA against G9a (e.g., G9a siRNA (human) (Santa Cruz Biotechnology) and others), etc.], L-channel calcium agonist (for example, Bayk8644) (Cell Stem Cell, 3, 568-574 (2008)), p53 inhibitors (for example, siRNA and shRNA against p53 (Cell Stem Cell, 3, 475-479 (2008)), UTF1 (Cell Stem Cell, 3, 475-479 (2008)), Wnt Signaling (for example, soluble Wnt3a) (Cell Stem Cell, 3, 132-135 (2008)), 2i/LIF (the 2i is an inhibitor of mitogen-activated protein kinase signaling and glycogen synthase kinase-3, PloS Biology, 6(10), 2237-2247 (2008)), ES cell-specific miRNA (for example, miR-302-367 cluster (Mol. Cell. Biol. doi: 10.1128/MCB.00398-08), miR-302 (RNA (2008) 14: 1-10), miR-291-3p, miR-294 and miR-295 (these are disclosed in Nat. Biotechnol. 27: 459-461 (2009))), but are not limited thereto. In the above description, the nucleic acid expression inhibitors may be in the form of expression vectors containing DNAs encoding siRNA or shRNA. (All the documents mentioned in this paragraph are herein incorporated by reference.)

Among the above factors constituting the nuclear reprogramming factors, for example, SV40 large T can also be included in the category of a factor for improving iPS cell generation efficiency from the viewpoint that they are not essential for nuclear reprogramming of somatic cells but are auxiliary factors. In the current situation that the mechanism of the nuclear reprogramming is unclear, whether the auxiliary factor other than factors essential for the nuclear reprogramming step is classified as a nuclear reprogramming factor or as a factor for improving iPS cell generation efficiency may be made conveniently. Thus, the nuclear reprogramming process of the somatic cells is recognized as an overall event resulting from the contact of a combination of nuclear reprogramming factors and one or more factors for improving iPS cell generation efficiency with the somatic cells, and therefore, those skilled in the art do not necessarily have a need to clearly distinguish both types of factors.

The contact of a factor for improving iPS cell generation efficiency with somatic cells can be carried out, depending on cases in which the factor is (a) a protein factor, (b) a nucleic acid encoding the protein factor, or (c) a low molecular compound, by a method similar to that described above for the Myc variant of the present invention as well as for the combination of nuclear reprogramming factors.

The nucleic acid encoding the Myc variant of the present invention and/or one or more factors for improving iPS cell generation efficiency other than the Myc variant of the present invention may be contacted with the somatic cells concomitantly with the combination of nuclear reprogramming factors, or either one of these combinations of factors may be contacted firstly with the somatic cells, so far as iPS cell generation efficiency from the somatic cells is significantly improved as compared with the efficiency in the absence of the combination of factors for improving iPS cell generation efficiency. In an embodiment, for example, when the combination of nuclear reprogramming factors is a combination of nucleic acids encoding the protein factors and the factor for improving iPS cell generation efficiency other than the Myc variant of the invention is a chemical inhibitor, the former factors require a certain period of time before the protein factors are expressed in large amounts after the nucleic acids are introduced into the cells, while the latter factor can rapidly act on the cells. Accordingly, the chemical inhibitor used as a factor for improving iPS cell generation efficiency can be added to the medium after the cells are cultured for a certain period of time following the gene-introducing treatment. In another embodiment, for example, when both the nuclear reprogramming factors and the factor for improving iPS cell generation efficiency are nucleic acids and are introduced using viral or plasmid vectors, all of the nucleic acids may be introduced into cells concomitantly.

(e) Improvement of the Generation Efficiency by Employing a Specific Culture Condition It is possible to further improve the generation efficiency of iPS cells by culturing cells under a hypoxic condition in the nuclear reprogramming step of the somatic cells. In the present specification, the "hypoxic condition" means that oxygen concentration in the atmosphere when culturing cells is significantly lower than that in air. Specifically, a condition in which the oxygen concentration is lower than that in the atmosphere of 5-10% $CO_2$/95-90% air generally used in a conventional cell cultivation is preferably employed, and a condition is included in which the oxygen concentration in atmosphere is not greater than 18%, for example. Preferably, the oxygen concentration in the atmosphere is not greater than 15% (e.g., not greater than 14%, not greater than 13%, not greater than 12% and not greater than 11%), not greater than 10% (e.g., not greater than 9%, not greater than 8%, not greater than 7% and not greater than 6%), or not greater than 5% (e.g., not greater than 4%, not greater than 3% and not greater than 2%). Also, the oxygen concentration in atmosphere is preferably not less than 0.1% (e.g., not less than 0.2%, not less than 0.3% and not less than 0.4%), not less than 0.5% (e.g., not less than 0.6%, not less than 0.7%, not less than 0.8% and not less than 0.95%), or not less than 1% (e.g., not less than 1.1%, not less than 1.2%, not less than 1.3% and not less than 1.4%).

A procedure generating a hypoxic condition in cell culture environment is not limited to a particular one. A method of culturing cells in a $CO_2$ incubator allowing adjustment of the oxygen concentration may be the easiest and may be employed as a suitable example. The $CO_2$ incubator allowing adjustment of the oxygen concentration is available on the market from various manufacturers (for example, $CO_2$ incubators for hypoxic cultivation supplied by makers such as Thermo Scientific Co., Ikemoto Scientific Technology Co., Ltd., Juji Field Inc., and Wakenyaku Co., Ltd. can be used).

The time to start cell cultivation under a hypoxic condition is not limited to a particular one so far as improvement of iPS cell generation efficiency is not prevented as compared with the case using normal oxygen concentration (20%). The cultivation may be started before the contact of the Myc variant of the present invention and the combination of nuclear reprogramming factors with the somatic cells, concomitantly with the contact, or after the contact. For example, it is preferable to start the cultivation under a hypoxic condition immediately after the contact of the Myc variant of the present invention and the combination of nuclear reprogramming factors with somatic cells, or after a certain period of time from the contact, for example, after 1 to 10 days, e.g. after 2, 3, 4, 5, 6, 7, 8 or 9 days.

Also, the period to culture the cells under the hypoxic condition is not limited to a particular one so far as improvement of iPS cell generation efficiency is not prevented as compared with the case using normal oxygen concentration (20%). For example, the period may be not less than 3 days, not less than 5 days, not less than 7 days or not less than 10 days, and not more than 50 days, not more than 40 days, not more than 35 days or not more than 30 days, but is not limited thereto. Preferable period for culturing under the hypoxic condition also varies depending on the oxygen concentration in the atmosphere, and those skilled in the art can suitably adjust the culture period depending on the oxygen concentration used. In an embodiment, when the selection of candidate colonies of iPS cells is carried out using drug resistance as an indicator, it is preferable to restore the hypoxic condition to the normal oxygen concentration before starting the selection by drug.

Furthermore, preferable time to start cell cultivation under the hypoxic condition and preferable culture period also vary depending on the type of the combination of nuclear reprogramming factors used, the iPS cell generation efficiency when prepared under a condition of the normal oxygen concentration.

(f) Selection and Verification of iPS Cells

After the Myc variant of the present invention and the combination of nuclear reprogramming factors, and one or more factors for improving iPS cell generation efficiency other than the Myc variant of the present invention, if any, are contacted with the somatic cells, the cells can be cultured under a condition suitable for cultivation of ES cells, for example. In the case of mouse cells, a conventional medium supplemented with a leukemia inhibitory factor (LIF) as a differentiation-suppressing factor may be used for the cultivation. In the case of human cells, it is desirable to use a medium supplemented with a basic fibroblast growth factor (bFGF) and/or a stem cell factor (SCF) instead of LIF. In general, cells are preferably cultured in the co-presence of feeder cells such as mouse embryonic fibroblasts (MEF) which are treated by radiation or an antibiotic to stop cell division. Usually, STO cells are often used as the MEF, and SNL cells [McMahon, A. P. & Bradley, A. Cell 62, 1073-1085 (1990); this document is herein incorporated by reference] are often used for the induction of iPS cells. The co-cultivation with feeder cells may be started before the contact of the Myc variant of the present invention and the combination of nuclear reprogramming factors with the cells, at the time of the contact, or after the contact (for example, after 1-10 days).

The selection of candidate colonies of iPS cells can be carried out by using the drug resistance and reporter activity as an indicator or through the visual morphology observation. The former method uses, for example, recombinant somatic cells in which a drug resistance gene and/or a reporter gene are targeted at a locus of a gene, for example, Fbx15, Nanog or Oct3/4, and preferably Nanog or Oct3/4, highly expressing specifically in differentiated pluripotent cells are employed, and drug resistance- and/or reporter activity-positive colonies are selected. Such recombinant somatic cells include, for example, MEF or TTF derived from a mouse in which βgeo gene that encodes a fusion protein of β-galactosidase and neomycin phosphotransferase is knocked into the Fbx15 locus [Takahashi & Yamanaka, Cell, 126, 663-676 (2006); this document is herein incorporated by reference], or MEF or TTF derived from a transgenic mouse in which green fluorescent protein (GFP) gene and puromycin-resistant gene are integrated into the Nanog locus [Okita et al., Nature, 448, 313-317 (2007); this document is herein incorporated by reference]. On the other hand, candidate colonies can be selected by visual morphology observation, for example, according to Takahashi et al., Cell, 131, 861-872 (2007) (this document is herein incorporated by reference). Although using reporter cells is convenient and efficient for selecting iPS cells, colony selection by visual observation is desirable in view of safety for preparing iPS cells used in therapeutic purposes.

Verification of whether the cells of colonies selected are iPS cells can be carried out by confirming the cells are positive to the above described Nanog (or Oct3/4) reporter such as puromycin-resistance and GFP-protein or by visually observing the ES cell-like colony formation. In order to ensure further accuracy, however, it is also possible to carry out various tests such as alkaline phosphatase staining, analysis of expression of various ES cell-specific genes, and confirmation of teratoma formation after transplantation of the selected cells into mice.

when the nucleic acid encoding the Myc variant of the present invention is introduced into the somatic cells, the resulting iPS cells are novel cells different from previously known iPS cells since they contain the exogenous nucleic acid. In particular, when the exogenous nucleic acid is introduced into the somatic cells using a retrovirus, lentivirus or the like, the exogenous nucleic acid is usually integrated into the genome of the resulting iPS cells, and therefore, the exogenous nucleic acid is stably retained.

(g) Application of iPS Cells

The iPS cells generated as described above can be used for various purposes. For example, it is possible to induce differentiation of the iPS cells to various cells such as myocardial cells, blood cells, nerve cells, vascular endothelial cells and insulin-secreting cells utilizing differentiation inducing methods reported for pluripotent stem cells such as ES cells. For example, JP-A 2002-291469 discloses a method to differentiate the cells into neural stem cells, JP-A 2004-121165 discloses a method to differentiate the cells into pancreas stem-like cells, and WO99/064565 discloses a method to differentiate the cells into hematopoietic cells. In addition, WO01/062899 discloses a method to differentiate the cells thorough the formation of germ layer. (The above documents are herein incorporated by reference.) Accordingly, iPS cells induced from patient's own somatic cells or from somatic cells of the other person having an HLA type that is identical or substantially identical to the patient can be differentiated into desired cells (i.e., cells of a diseased organ of the patient, cells exerting a therapeutic effect on a disease) and the differentiated cells can be transplanted into the patient. Thus, a stem cell therapy with autologous transplantation becomes possible. Also, it is thought that functional cells such as hepatic cells differentiated from the iPS cells reflect the actual state of the functional cells in the living body more faithfully than existing cell lines corresponding to the cells, and therefore, they can be used suitably for in vitro screening to determine efficacy or toxicity of pharmaceutical candidate compounds.

The present invention is described more specifically referring to the following Examples, but it goes without saying that the present invention is not limited thereto.

EXAMPLES

The c-Myc, L-Myc, and variants thereof used in the following Examples and attached Drawings are represented as follows:

(c-Myc and L-Myc)

Human c-MYC: c-MYC, or c

Human L-MYC: L-MYC, L-MYC1, or L

Mouse c-Myc: c-Myc, or Ms-c

Mouse L-Myc: L-Myc, or Ms-L (Point Mutants of c-Myc and L-Myc)

Point mutant having substitution of Trp with Glu at position 136 of mouse c-Myc: Ms-c-W136E, or Ms-c136 (Point mutant having substitution of Trp with Glu at position 135 of human c-Myc: c-W135E, or c135)

Point mutant having substitution of Val with Asp at position 394 of mouse c-Myc: Ms-c-V394D, or Ms-c394

Point mutant having substitution of Leu with Pro at position 420 of mouse c-Myc: Ms-c-L420P, or Ms-c420

Point mutant having substitution of Trp with Glu at position 96 of mouse L-Myc: Ms-L-W96E, or Ms-L96

Point mutant having substitution of Val with Asp at position 325 of mouse L-Myc: Ms-L-V325D, or Ms-L325

Point mutant having substitution of Leu with Pro at position 351 of mouse L-Myc: Ms-L-L351P, or Ms-L351

All the above six point mutants are the same factors (the same genes) as the six point mutants described in Example 27 of International Publication WO2009/057831 and in Example 29 of US-A 2009/0227032.

As discussed in US-A 2009/0227032, Ms-c-W136E (c-MycW135E in the above publication) is a mutant of c-Myc having a mutation in the region essential for interaction with the nucleic acid factor which exerts an important action on the transformation activity of c-Myc (Brough et al., Molecular and-Cellular Biology 15(3): 1536-1544, 1995). Ms-c-V394D is a mutant losing an ability to bind to Miz-1 protein (Herold et al., Mol. Cell. 10(3): 509-21, 2002), and Ms-c-L420P is a mutant losing an ability to bind to Max protein (Blackwood et al., Science 251(4998): 1211-17, 1991). Ms-L-W96E, Ms-L-V325D and Ms-L-L351P are point mutants at positions corresponding to Ms-c-W136E, Ms-c-V394D and Ms-c-L420P, respectively. (All the documents mentioned in this paragraph are herein incorporated by reference.)

As described in the above publication, both c-Myc and L-Myc have an identity near 100% at the amino acid level between human and mouse. Also, even when mouse c-Myc and mouse L-Myc were used, human iPS colonies arose in the same manner as in human c-MYC and human L-MYC were used. Accordingly, mouse genes were used in the experiments as alternatives to the human genes. In this connection, the point mutations in human c-Myc and L-Myc corresponding to those in mouse factors are shown in the following Table 1. The mutated sites of these point mutants on the human amino acid sequence are as shown in FIG. 1.

TABLE 1

| Type | Mouse | Human |
|---|---|---|
| c-Myc | W136E | W135E |
| c-Myc | V394D | V394D |
| c-Myc | L420P | L420P |
| L-Myc | W96E | W96E |
| L-Myc | V325D | V321D |
| L-Myc | L351P | L347P |

(Variants of Human c-MYC having N-terminal Deletion)

Variant having an amino acid sequence at and after position 14 in the human c-MYC amino acid sequence: cdN1

Variant having an amino acid sequence at and after position 42 in the human c-MYC amino acid sequence: cdN2

Variant having an amino acid sequence at and after position 65 in the human c-MYC amino acid sequence: cdN3

Variant having an amino acid sequence at and after position 83 in the human c-MYC amino acid sequence: cdN4

Variant having an amino acid sequence at and after position 108 in the human c-MYC amino acid sequence: cdN5

Variant having an amino acid sequence at and after position 128 in the human c-MYC amino acid sequence: cdN6

Variant having an amino acid sequence at and after position 141 in the human c-MYC amino acid sequence: cdN7

The N-terminal start sites of these deletion mutants are as shown in FIG. 1.

(Variants of Human c-W135E having N-terminal Deletion)

Combination variant of human c-W135E with cdN1: c135dN1

Combination variant of human c-W135E with cdN2: c135dN2

Combination variant of human c-W135E with cdN3: c135dN3

Combination variant of human c-W135E with cdN4: c135dN4

Combination variant of human c-W135E with cdN5: c135dN5

Combination variant of human c-W135E with cdN6: c135dN6

(Variants of Human L-MYC having N-terminal Deletion)

Variant having an amino acid sequence at and after position 22 in the human L-MYC amino acid sequence: LdN2

Variant having an amino acid sequence at and after position 45 in the human L-MYC amino acid sequence: LdN4

Variant having an amino acid sequence at and after position 70 in the human L-MYC amino acid sequence: LdN5

Variant having an amino acid sequence at and after position 89 in the human L-MYC amino acid sequence: LdN6

Variant having an amino acid sequence at and after position 102 in the human L-MYC amino acid sequence: LdN7

The N-terminal start sites of these deletion mutants are as shown in FIG. 1.

(Three Factors)

Three factors of OCT3/4, KLF4 and SOX2 derived from human are designated as "3F".

Example 1

Study on Induction of iPS Cells with a Variant of c-MYC having N-terminal Deletion 1) Preparation of Retroviral Vectors Encoding Variants of Human c-MYC having N-terminal Deletion Retroviral vectors encoding variants cdN1 to cdN7 of human c-MYC having N-terminal deletion were prepared. Firstly, fragments were amplified by PCR using human c-MYC cDNA as a template and the following sets of primers.

<Forward Primers>

```
                                    (SEQ ID NO: 11)
dN1-s       CACCATGCTCGACTACGACTCGGTGCAGCC

                                    (SEQ ID NO: 12)
dN2-s       CACCATGCCCCCGGCGCCCAGCGAGGATAT

                                    (SEQ ID NO: 13)
dN3-s       CACCATGCGCCGCTCCGGGCTCTGCTCGCC

                                    (SEQ ID NO: 14)
dN4-s       CACCATGCGGGGAGACAACGACGGCGGTGG

                                    (SEQ ID NO: 15)
dN5-s       CACCATGGGAGACATGGTGAACCAGAGTTT

                                    (SEQ ID NO: 16)
dN6-s       CACCATGATCATCATCCAGGACTGTATGTG

                                    (SEQ ID NO: 17)
dN7-s       CACCATGGCCGCCAAGCTCGTCTCAGAGAA
```

<Reverse Primers (Common to all Fragments)>

```
                                    (SEQ ID NO: 18)
HsMyc-AS    TCACGCACAAGAGTTCCGTAGCTGTTCAAG
```

The LR reaction between pENTR-D-TOPO-cdN1 to cdN7, which were obtained by cloning each of the resulting fragments into pENTR-D-TOPO (Invitrogen), and retroviral vector pMXs-gw (presented by Dr. Toshio Kitamura of the University of Tokyo; Exp. Hematol. 31; 1007-1014, 2003) (this document is herein incorporated by reference) to prepare pMXs-cdN1 to cdN7.

2) Verification of Expression with Western Blotting

Figures 2, 4:
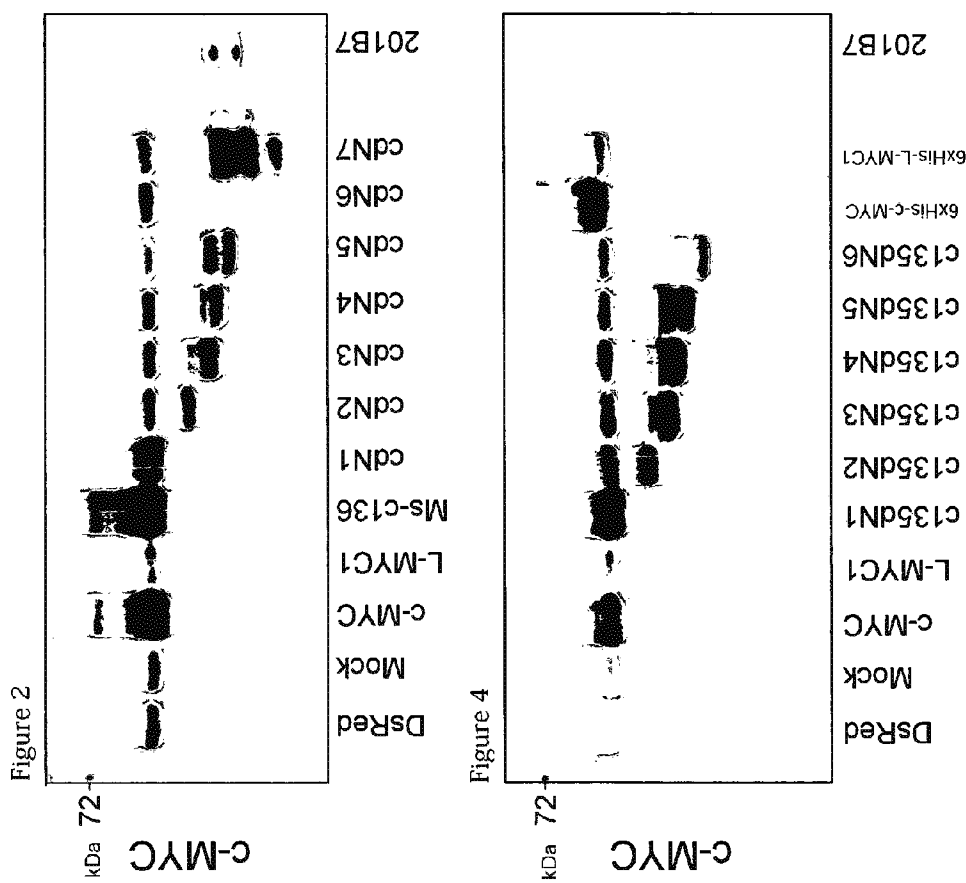
FIG. 2 is a photograph showing the results obtained by detecting c-Myc protein (endogenous, exogenous) with western blotting. Samples as shown in Example 1-2) were used. The name of each factor used is indicated under each lane. In the Figure, "201B7" represents iPS cells (Cell, 131, 861-872 (2007); this document is herein incorporated by reference).
FIG. 4 is a photograph showing the results obtained by detecting the c-Myc protein (endogenous, exogenous) with western blotting. Samples as shown in Example 2-2 were used. The name of each factor used is shown under each lane. In this Figure, "6xHis-c-MYC" represents c-MYC with a His tag, "6xHis-L-MYC1" represents L-MYC with a His tag, and "201B7" represents iPS cells (Cell, 131, 861-872 (2007)).

The retroviral vectors pMXs-cdN1 to cdN7 were individually introduced into Plat-E cells (Morita, S. et al., Gene Ther. 7, 1063-1066) according to Cell, 131: 861-872 (2007) (this document is herein incorporated by reference). Two days after cultivation, the Plat-E cells were treated with 1×SDS sample buffer and then boiled for 10 minutes to obtain samples for electrophoresis. Then, western blotting was carried out by a conventional method using anti-c-Myc antibody (a product of Santa Cruz) as the primary antibody and HRP-linked anti-rabbit IgG antibody (a product of CST) as the secondary antibody. The results are shown in FIG. 2. From the fact that a band of endogenous c-MYC (an upper band in each lane of cdN1 to cdN7) and also a band having a size corresponding to each variant were detected in each sample, the expression of each variant was verified.

3) Induction of iPS Cells

Fibroblasts derived from human adult skin expressing a mouse ecotropic virus receptor Slc7a1 gene (aHDF-Slc7a1) were prepared according to Cell, 131, 861-872 (2007). The aHDF-Slc7a1 cells were seeded on a 6-well plate in a proportion of $1\times10^5$ cells per well. The next day, a total of four genes consisting of three genes of OCT3/4, KLF4, and SOX2 that were derived from human and each variant having N-terminal deletion prepared in the above 1) were retrovirally introduced into the cells according to Cell, 131, 861-872 (2007) (in FIG. 3, 3F-cdN1 to 3F-cdN7). In addition, a total of four genes consisting of the above three genes of OCT3/4, KLF4, and SOX2 that were derived from human and each gene of the point mutants were retrovirally introduced into the cells(in FIG. 3, 3F-Ms-c136, 3F-Ms-c394, 3F-Ms-c420, 3F-Ms-L96, 3F-Ms-L325, and 3F-Ms-L351).

The aHDF-Slc7a1 cells were infected with each of the above retroviruses, cultured, recovered after 6 days, and again seeded on MSTO cells ($5\times10^5$ cells/100 mm dish). From the next day, the culture medium was replaced with the medium for culturing primate ES cells (ReproCELL) supplemented with 4 ng/ml recombinant human bFGF (WAKO).

Figure 3:
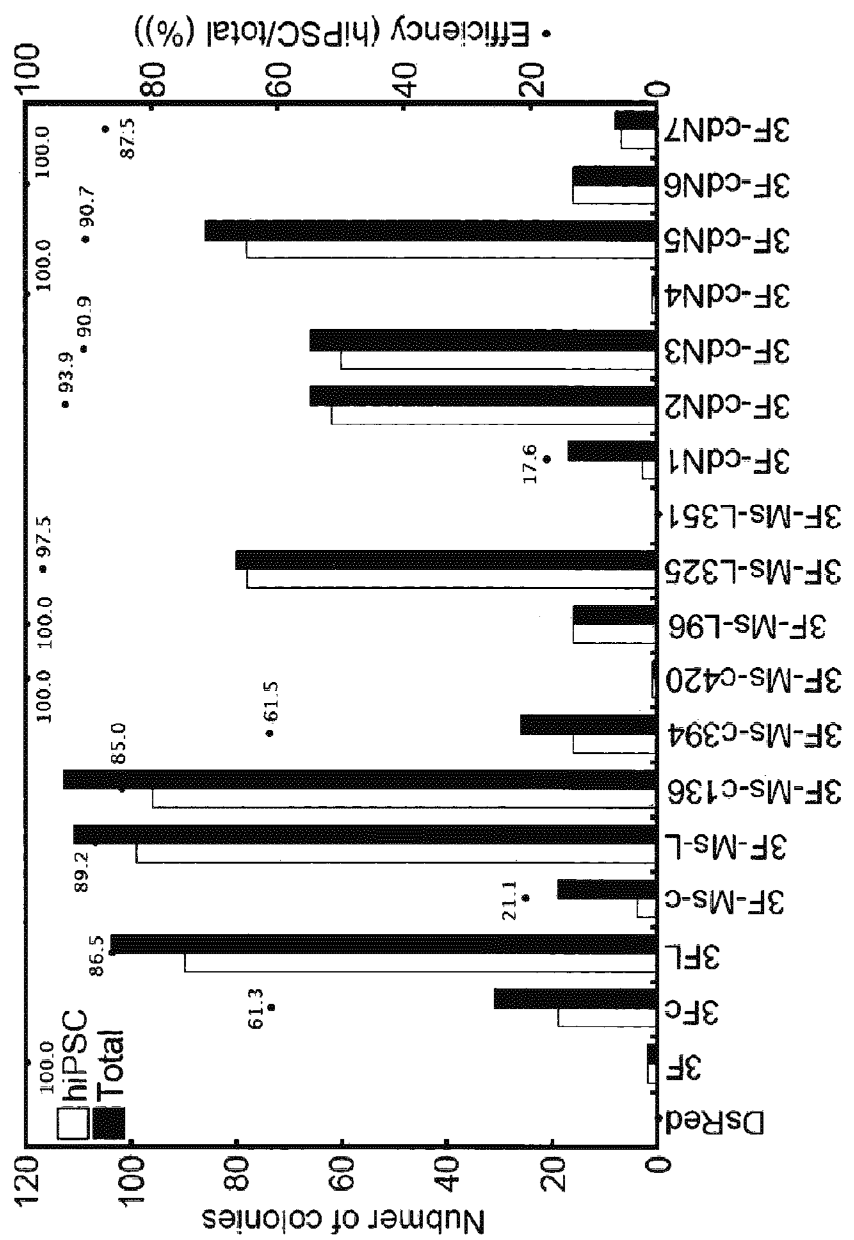
FIG. 3 is a graph showing the result obtained by counting the number of colonies of human iPS cells generated by retrovirally introducing the genes of the factors as shown under each graph (each factor as described in Example 1-3) into aHDF-Slc7a1 cells. The black bar represents the total number of colonies, and the white bar represents the number of colonies of iPS cells. The numerical value on each graph represents the percentage (%) of the number of colonies of iPS cells to the total number of colonies.

The number of human iPS cell colonies (ES-like colonies) generated on the thirty-first day after the retroviral infection was counted. The results are shown in FIG. 3. As shown in FIG. 3, 3F-cdN2, 3F-cdN3 and 3F-cdN5 showed a remarkable increase of the number of human iPS cell colonies (increase of iPS induction activity), and also an increase of the percentage of the number of iPS cell colonies to the total number of colonies, as compared with four genes (3Fc) of OCT3/4, KLF4, SOX2 and c-MYC. On the other hand, 3F-cdN1 showed a very low number of iPS cell colonies, and therefore, it was presumed that a region acting negatively on the induction of iPS cells is present in a region of N-terminal side of the dN2 start site in the amino acid sequence of c-MYC (region at positions 1 to 41 in human c-MYC).

Also, 3F-cdN4 showed very few colonies, and therefore, it was presumed that a region acting positively on the induction of iPS cells is present at positions 65 to 82 in human c-MYC. However, this also suggested a possibility that the deletion of the region caused a significant change in a higher-order structure of c-MYC and the effects could not be observed.

In addition, 3FL, 3F-Ms-L, 3F-Ms-c136 and 3F-Ms-L325 showed a remarkable increase of the number of human iPS colonies (increase of iPS induction activity), and also an increase of the percentage of the number of iPS colonies to the total number of colonies, as compared with the 3Fc.

Example 2

Investigation of Induction of iPS Cells with a Variant of Human c-W135E having N-terminal Deletion 1) Preparation of Retroviral Vectors Encoding Variants of Human c-W135E having N-terminal Deletion Point mutation of human W135E was introduced by carrying out PCR using pENTR-D-TOPO-cdN1 to cdN6 constructed in Example 1-1) as a template and using primers [OLIGO1: CAGGACTGTATGGAGAGCGGTTTCT (SEQ ID NO:19); and OLIGO2: AGAAACCGCTCTCCATACAGTCCTG (SEQ ID NO:20)]. After the point mutation was verified by sequencing, the LR reaction with retroviral vector pMXs-gw was carried out to prepare pMXs-c135dN1 to c135dN6.

2) Verification of Expression with Western Blotting

The retroviral vectors pMXs-c135dN1 to c135dN6 were individually introduced into Plat-E cells, in the same manner as in Example 1-2). Then, western blotting was carried out by a conventional method using a lysate of the Plat-E cells. The results are shown in FIG. 4. From the fact that a band of endogenous c-MYC (an upper band in each lane of c135dN1 to c135dN6) and also a band having a size corresponding to each variant were detected in each sample, the expression of each variant was verified.

3) Induction of iPS Cells

Figure 5:
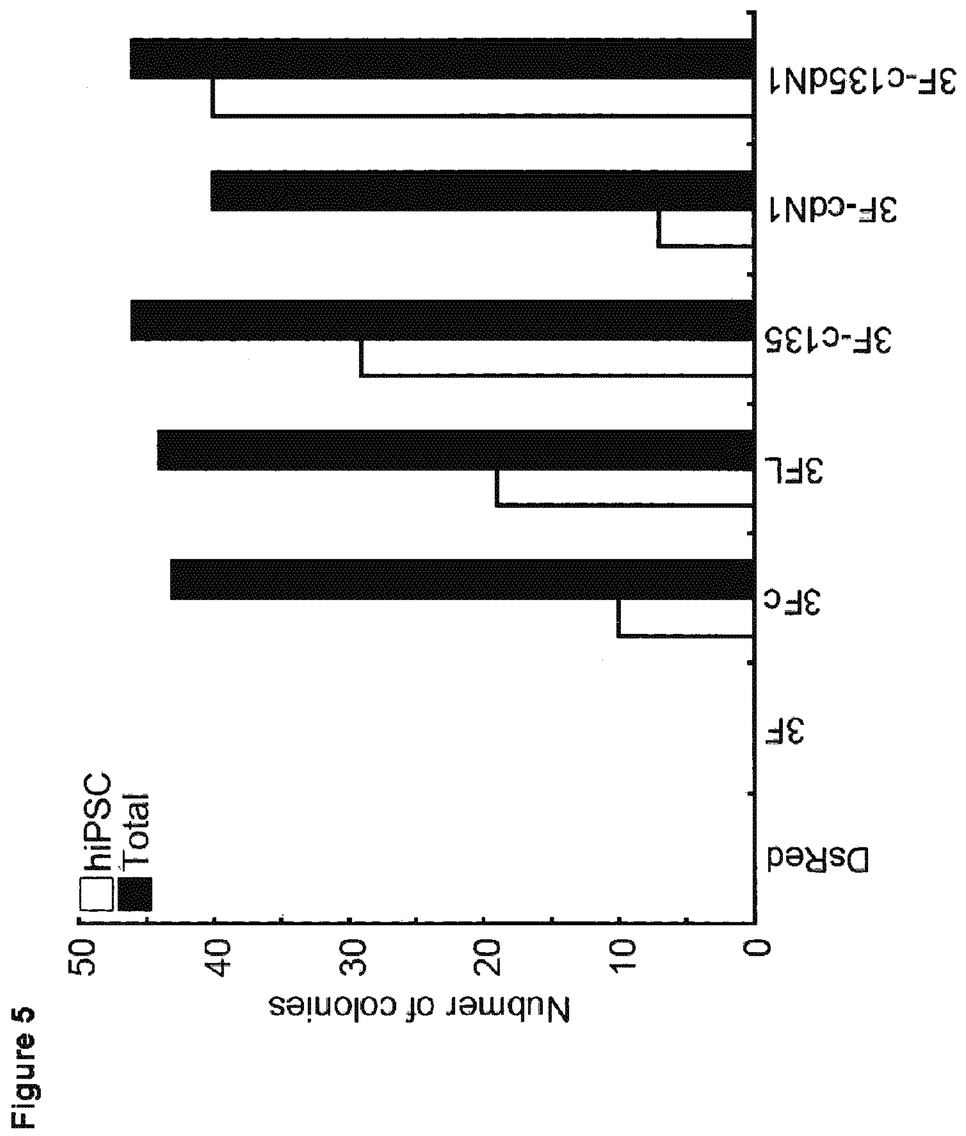
FIG. 5 is a graph showing the results obtained by counting the number of colonies of human iPS cells generated by retrovirally introducing the gene of the factor as shown under each graph into aHDF-Slc7a1 cells. The black bar represents the total number of colonies, and the white bar represents the number of colonies of iPS cells.

A total of four genes consisting of three genes derived from human (OCT3/4, KLF4, and SOX2) and any one of c135dN1 to c135dN6 prepared in the above 1 were retrovirally introduced in the same manner as in Example 1. The number of human iPS colonies (ES-like colonies) generated on the thirtieth day after the retroviral infection was counted. The results are shown in FIG. 5. As in Example 1, 3F-cdN1 showed a very low number of iPS colonies, while the introduction of point mutation at position 135 in c-MYC, which is presumed to be relevant to transformation of cells, drastically increased the number of iPS colonies, and also increased the percentage of the number of iPS colonies to the total number of colonies (3F-c135dN1 in FIG. 5). On the other hand, a remarkable iPS induction activity of 3F-c135dN2 to 3F-c135dN6 was not recognized in the present experiments.

Example 3

Investigation of Induction of iPS Cells with Variants of L-MYC Derivatives having N-terminal Deletion 1) Preparation of Retroviral Vectors Encoding Variants of Human L-MYC having N-terminal Deletion Retroviral vectors encoding variants LdN2, LdN4, LdN5, LdN6 and LdN7 of human L-MYC having N-terminal deletion were prepared (excepting L-MYC variants corresponding to cdN1 and cdN3; see FIG. 1). Firstly, fragments were amplified by PCR using human L-MYC cDNA as a template and using the following sets of primers.

<Forward Primers>

```
                                                  (SEQ ID NO: 21)
LMyc-dN2-s    CACCATGTCCACGGCGCCCAGCGAGGACAT

                                                  (SEQ ID NO: 22)
LMyc-dN4-s    CACCATGTGGGGCTTGGGTCCCGGCGCAGG

                                                  (SEQ ID NO: 23)
LMyc-dN5-s    CACCATGGGAGACGAAGCGGAATCCCGGGG

                                                  (SEQ ID NO: 24)
LMyc-dN6-s    CACCATGATCATACGCCGTGACTGCATGTG

                                                  (SEQ ID NO: 25)
LMyc-dN7-s    CACCATGCGGGAACGGCTGGAGAGAGCTGT
```

<Reverse Primers (Common to all Fragments)>

```
                                                  (SEQ ID NO: 26)
Hu-L-Myc-as2    TTAGTAGCCAGTGAGGTATGCAATTC
```

The LR reaction was carried out between pENTR-D-TOPO-LdN2, -LdN4, -LdN5, -LdN6 and -LdN7, which were obtained by cloning each of the resulting fragments into pENTR-D-TOPO (Invitrogen), and retroviral vector pMXs-gw to prepare pMXs-LdN2, -LdN4, -LdN5, -LdN6 and -LdN7.

2) Induction of iPS Cells

Figure 6:
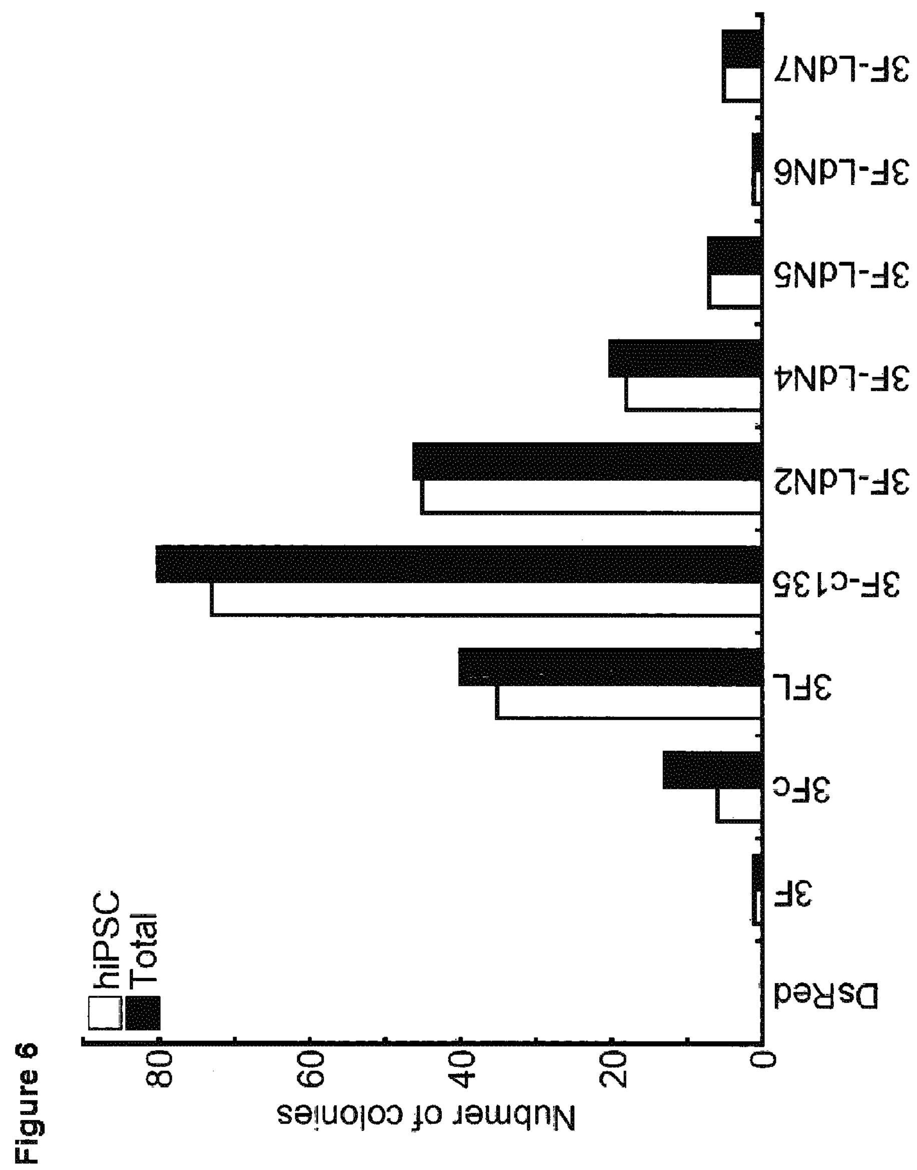
FIG. 6 is a graph showing the results obtained by counting the number of colonies of human iPS cells generated by retrovirally introducing the gene of the factor as shown under each graph into aHDF-Slc7a1 cells. The black bar represents the total number of colonies, and the white bar represents the number of colonies of iPS cells.

A total of four genes consisting of three genes derived from human (OCT3/4, KLF4, and SOX2) and any one of LdN2, LdN4, LdN5, LdN6 and LdN7 prepared in the above 1) were retrovirally introduced in the same manner as in Example 1. The number of human iPS colonies (ES-like colonies) generated on the thirty-ninth day after the retroviral infection was counted. The results are shown in FIG. 6. It was found that increasing deletion of the N-terminus of L-MYC1 decreased the number of iPS colonies. Also, 3F-LdN2 and 3F-LdN4 showed an increase of the number of human iPS colonies (increase of iPS induction activity), and also an increase of the percentage of the number of iPS colonies to the total number of colonies, as compared with the 3Fc.

The present experiments suggested that the region important for iPS induction activity is present between dN2 and dN5 because the activity notably decreased in the deletion after LdN5.

Example 4

Investigation of Transformation Activity

It is reported that c-Myc has a transformation activity, while L-Myc has a very low transformation activity as compared with that of c-Myc (about 1 to 10% of c-Myc) (Birrer et al., Molecular and Cellular Biology 8: 2668-2673, 1988; and Barrett et al., Molecular and Cellular Biology 12: 3130-3137, 1992). Also, it has been presumed that position 136 of c-Myc is involved in transformation of cells (Brough et al., Molecular and Cellular Biology 15(3): 1536-1544, 1995). (All the documents mentioned in this paragraph are herein incorporated by reference.)

Accordingly, the present inventors investigated whether the variants prepared have a transformation activity.

Figure 7:
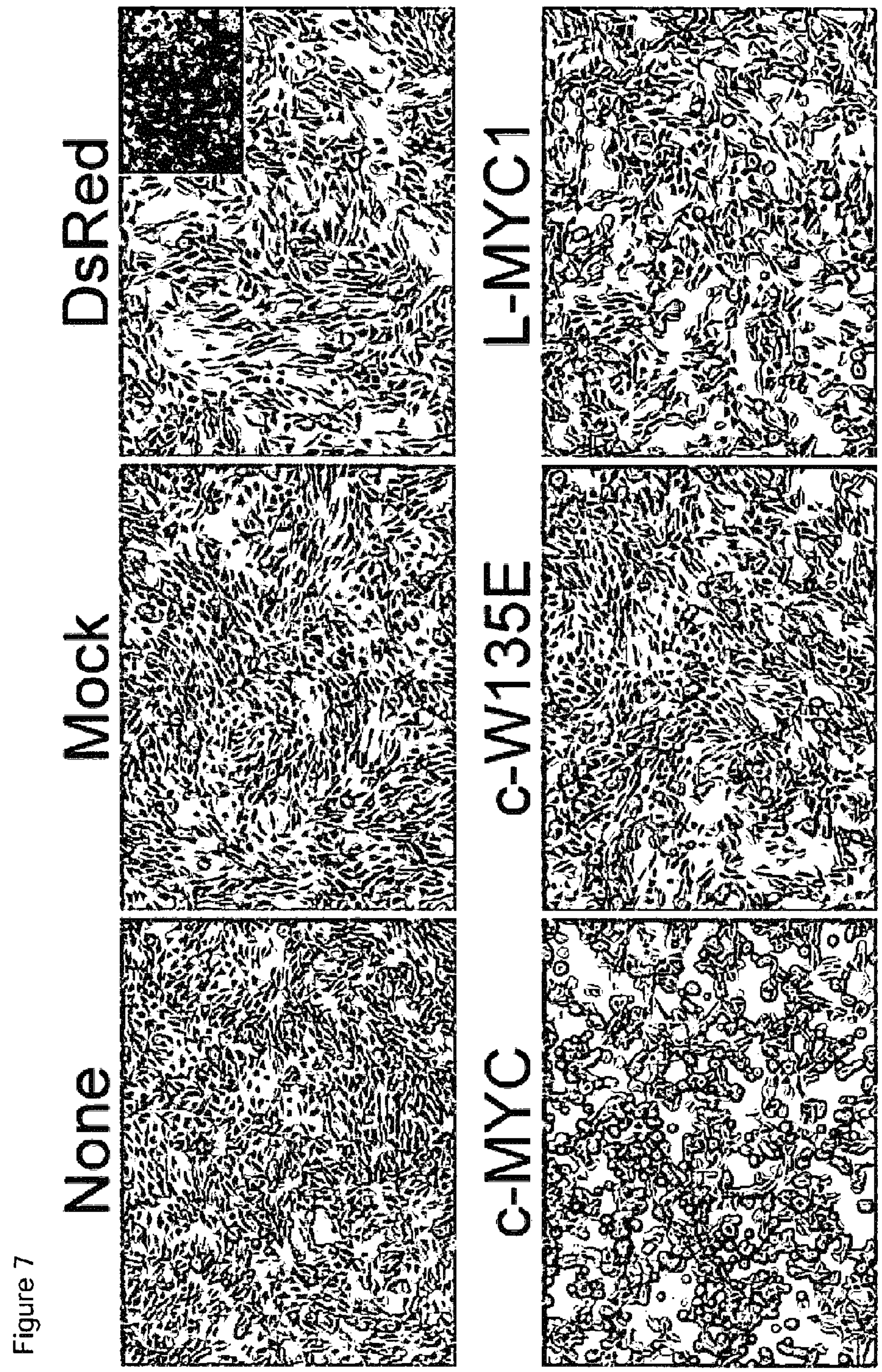
FIG. 7 is a photograph showing the results obtained by retrovirally introducing each gene as shown in Example 4 into mouse NIH3T3 cells, and observing the activity to transform the cells.
Figure 8:
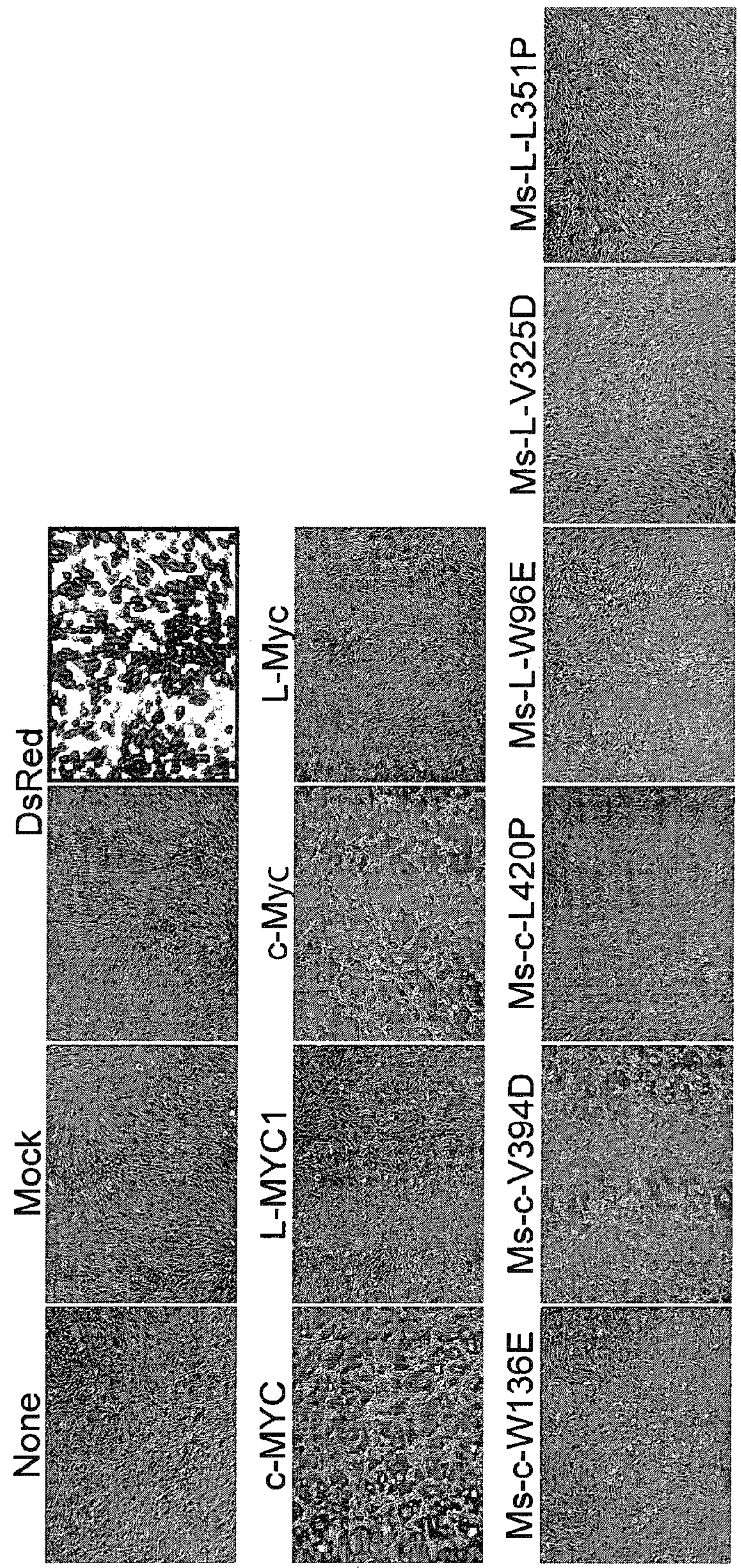
FIG. 8 is a photograph showing the results obtained by retrovirally introducing each gene as shown in Example 4 into mouse NIH3T3 cells, and observing the activity to transform the cells.
Figure 9:
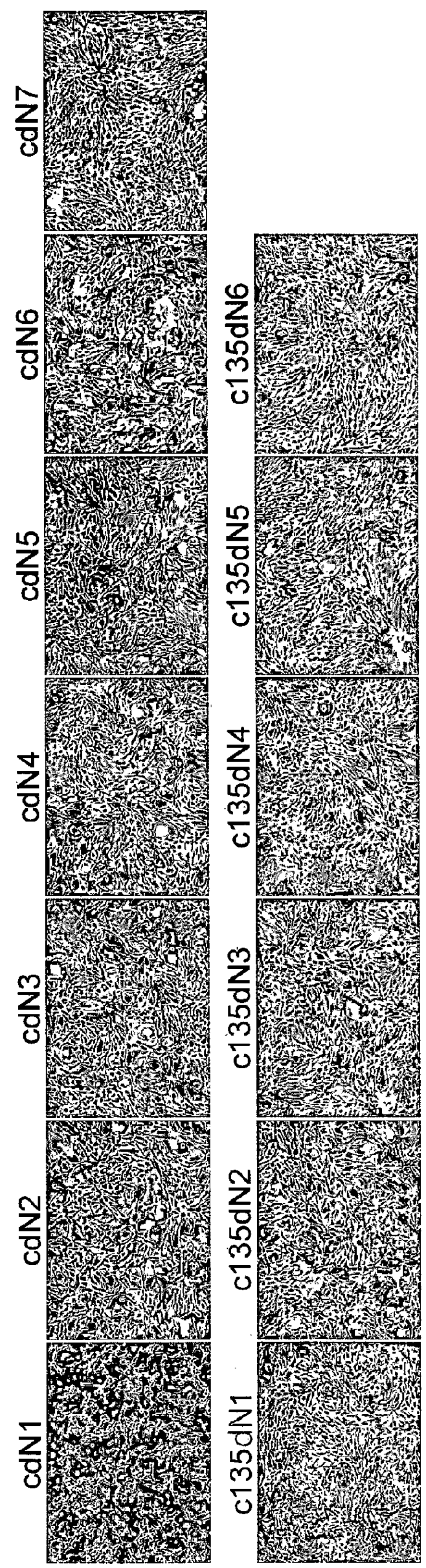
FIG. 9 is a photograph showing the results obtained by retrovirally introducing each gene as shown in Example 4 into mouse NIH3T3 cells with a retrovirus, and observing the activity to transform the cells.

Mouse NIH3T3 cells were seeded on a 6-well plate in a proportion of $1\times10^5$ cells per well. The next day, the following genes derived from human: c-MYC, c-W135E, L-MYC, cdN1 to cdN7, and c135dN1 to c135dN6; and the following genes derived from mouse: c-Myc, L-Myc, Ms-c-W136E, Ms-c-V394D, Ms-c-L420P, Ms-L-W96E, Ms-L-V325D, and Ms-L-L351P were introduced with a retrovirus according to a method described in Cell, 126, 663-676 (2006) (this document is herein incorporated by reference). Two days after the introduction, morphology of cells was observed. The results are shown in FIG. 7 to FIG. 9. c-MYC (c-Myc) had a transformation activity relative to NIH3T3 cells, while c-W135E (FIG. 7), Ms-c-W136E, and Ms-c-L420P (FIG. 8) lost the transformation activity. Also, L-MYC (L-MYC1, L-Myc) (FIG. 7, FIG. 8) and point mutants thereof (in FIG. 8, Ms-L-W96E, Ms-L-V325D, Ms-L-L351P) did not have the transformation activity. In the variants of c-MYC having N-terminal deletion, cdN1 had a transformation activity, but lost the transformation activity by mutating position 135 (c135dN1 in FIG. 9). Also, any of cdN2 to cdN7 and c135dN2 to c135dN6 did not have the transformation activity (FIG. 9).

As is apparent from the above Examples 1 to 4, L-MYC having a low (almost no) transformation activity as well as its variants [V325D (V321D), LdN2, and LdN4] and c-MYC variants losing the transformation activity [W135E (W136E), cdN2, cdN3, cdN5, and c135dN1] have a tendency toward an elevated iPS induction activity as compared with c-Myc having a transformation activity. Thus, it was shown that the transformation activity of Myc acts rather negatively on the induction of human iPS cells.

What is claimed is:

1. A method for improving induced pluripotent stem (iPS) cell generation efficiency, which comprises;

a) introducing into somatic cells nuclear reprograming factors comprising Oct3/4, Sox2 and a Myc variant, wherein the reprogramming factor is a reprogramming factor protein or nucleic acid encoding the reprogramming factor protein, wherein the Myc variant has the following features (1) and (2):

(1) having an activity to improve iPS cell generation efficiency which is comparative to, or greater than that of c-Myc; and (2) having a transformation activity which is lower than that of c-Myc; and b) culturing the somatic cells comprising said nuclear reprogramming factors to produce iPS cells.

2. The method according to claim 1, wherein the somatic cells are derived from one or more humans.

3. The method according to claim 1, wherein the activity of the Myc variant to transform NIH3T3 cells is lower than that of c-Myc.

4. The method according to claim 1, wherein the Myc variant is the c-Myc variant and wherein the c-Myc variant has entire or partial deletion of amino acids at positions 1 to 41 in the amino acid sequence of human c-Myc as shown in SEQ ID NO:2.

5. The method according to claim 4, wherein the c-Myc variant is any one of the following variants (1) to (4):

(1) a variant having deletion of amino acids at positions 1 to 41 in the amino acid sequence of human c-Myc as shown in SEQ ID NO:2, (2) a variant having deletion of amino acids at positions 1 to 64 in the amino acid sequence of human c-Myc as shown in SEQ ID NO:2, (3) a variant having deletion of amino acids at positions 1 to 107 in the amino acid sequence of human c-Myc as shown in SEQ ID NO:2, (4) a variant having deletion of amino acids at positions 1 to 13 and having a mutation at position 135 in the amino acid sequence of human c-Myc as shown in SEQ ID NO:2.

6. The method according to claim 1, wherein the Myc variant is the c-Myc variant and wherein the c-Myc variant has a mutation at position 135 in the amino acid sequence of human c-Myc as shown in SEQ ID NO:2.

7. The method according to claim 5, wherein the mutation at position 135 in the SEQ ID NO:2 is substitution or deletion of the amino acid.

8. The method according to claim 7, wherein Trp at position 135 in the SEQ ID NO:2 is substituted with Glu or Gly.

9. The method according to claim 1, wherein the Myc variant is the L-Myc variant and wherein the L-Myc variant has at least an amino acid sequence at and after position 70 in the amino acid sequence of human L-Myc as shown in SEQ ID NO:6.

10. The method according to claim 9, wherein the L-Myc variant is either the following variant (1) or (2):

(1) a variant having at least amino acids at and after position 45 in the amino acid sequence of human L-Myc as shown in SEQ ID NO:6, (2) a variant having at least amino acids at and after position 22 in the amino acid sequence of human L-Myc as shown in SEQ ID NO:6.

11. The method according to claim 1, wherein the Myc variant is the L-myc variant and wherein the L-Myc variant has a mutation at position 321 in the amino acid sequence of human L-Myc as shown in SEQ ID NO:6.

12. The method according to claim 11, wherein the mutation at position 321 in the SEQ ID NO:6 is substitution or deletion.

13. The method according to claim 12, wherein Val at position 321 in the SEQ ID NO:6 is substituted with Asp.

14. A method for preparing iPS cells, which comprises a step of introducing a Myc variant wherein the Myc variant is a c-Myc variant an N-Myc variant or an L-Myc variant, and wherein the Myc variant has the following features (1) and (2):

(1) having an activity to improve iPS cell generation efficiency which is comparative to, or greater than that of c-Myc; and (2) having a transformation activity which is lower than that of c-Myc;

or a nucleic acid encoding the variant, and a combination of one or more nuclear reprogramming factors into somatic cells.

* * * * *

SEQUENCE LISTING

```
<160> NUMBER OF SEQ ID NOS: 26

<210> SEQ ID NO 1
<211> LENGTH: 2379
<212> TYPE: DNA
<213> ORGANISM: Homo Sapience
<220> FEATURE:
<221> NAME/KEY: CDS
<222> LOCATION: (571)..(1890)

<400> SEQUENCE: 1

gacccccgag ctgtgctgct cgcggccgcc accgccgggc cccggccgtc cctggctccc      60

ctcctgcctc gagaagggca gggcttctca gaggcttggc gggaaaaaga acggagggag     120

ggatcgcgct gagtataaaa gccggttttc ggggctttat ctaactcgct gtagtaattc     180

cagcgagagg cagagggagc gagcgggcgg ccggctaggg tggaagagcc gggcgagcag     240

agctgcgctg cgggcgtcct gggaagggag atccggagcg aatagggggc ttcgcctctg     300

gcccagccct cccgctgatc ccccagccag cggtccgcaa cccttgccgc atccacgaaa     360

ctttgcccat agcagcgggc gggcactttg cactggaact tacaacaccc gagcaaggac     420

gcgactctcc cgacgcgggg aggctattct gcccatttgg ggacacttcc ccgccgctgc     480

caggacccgc ttctctgaaa ggctctcctt gcagctgctt agacgctgga tttttttcgg     540

gtagtggaaa accagcagcc tcccgcgacg atg ccc ctc aac gtt agc ttc acc      594
                                 Met Pro Leu Asn Val Ser Phe Thr
                                 1               5

aac agg aac tat gac ctc gac tac gac tcg gtg cag ccg tat ttc tac      642
Asn Arg Asn Tyr Asp Leu Asp Tyr Asp Ser Val Gln Pro Tyr Phe Tyr
    10                  15                  20

tgc gac gag gag gag aac ttc tac cag cag cag cag cag agc gag ctg      690
Cys Asp Glu Glu Glu Asn Phe Tyr Gln Gln Gln Gln Gln Ser Glu Leu
25                  30                  35                  40

cag ccc ccg gcg ccc agc gag gat atc tgg aag aaa ttc gag ctg ctg      738
Gln Pro Pro Ala Pro Ser Glu Asp Ile Trp Lys Lys Phe Glu Leu Leu
                45                  50                  55

ccc acc ccg ccc ctg tcc cct agc cgc cgc tcc ggg ctc tgc tcg ccc      786
Pro Thr Pro Pro Leu Ser Pro Ser Arg Arg Ser Gly Leu Cys Ser Pro
            60                  65                  70

tcc tac gtt gcg gtc aca ccc ttc tcc ctt cgg gga gac aac gac ggc      834
Ser Tyr Val Ala Val Thr Pro Phe Ser Leu Arg Gly Asp Asn Asp Gly
        75                  80                  85

ggt ggc ggg agc ttc tcc acg gcc gac cag ctg gag atg gtg acc gag      882
Gly Gly Gly Ser Phe Ser Thr Ala Asp Gln Leu Glu Met Val Thr Glu
    90                  95                  100

ctg ctg gga gga gac atg gtg aac cag agt ttc atc tgc gac ccg gac      930
Leu Leu Gly Gly Asp Met Val Asn Gln Ser Phe Ile Cys Asp Pro Asp
105                 110                 115                 120
```

-continued

```
gac gag acc ttc atc aaa aac atc atc atc cag gac tgt atg tgg agc      978
Asp Glu Thr Phe Ile Lys Asn Ile Ile Ile Gln Asp Cys Met Trp Ser
                125                 130                 135

ggc ttc tcg gcc gcc gcc aag ctc gtc tca gag aag ctg gcc tcc tac     1026
Gly Phe Ser Ala Ala Ala Lys Leu Val Ser Glu Lys Leu Ala Ser Tyr
            140                 145                 150

cag gct gcg cgc aaa gac agc ggc agc ccg aac ccc gcc cgc ggc cac     1074
Gln Ala Ala Arg Lys Asp Ser Gly Ser Pro Asn Pro Ala Arg Gly His
        155                 160                 165

agc gtc tgc tcc acc tcc agc ttg tac ctg cag gat ctg agc gcc gcc     1122
Ser Val Cys Ser Thr Ser Ser Leu Tyr Leu Gln Asp Leu Ser Ala Ala
    170                 175                 180

gcc tca gag tgc atc gac ccc tcg gtg gtc ttc ccc tac cct ctc aac     1170
Ala Ser Glu Cys Ile Asp Pro Ser Val Val Phe Pro Tyr Pro Leu Asn
185                 190                 195                 200

gac agc agc tcg ccc aag tcc tgc gcc tcg caa gac tcc agc gcc ttc     1218
Asp Ser Ser Ser Pro Lys Ser Cys Ala Ser Gln Asp Ser Ser Ala Phe
                205                 210                 215

tct ccg tcc tcg gat tct ctg ctc tcc tcg acg gag tcc tcc ccg cag     1266
Ser Pro Ser Ser Asp Ser Leu Leu Ser Ser Thr Glu Ser Ser Pro Gln
            220                 225                 230

ggc agc ccc gag ccc ctg gtg ctc cat gag gag aca ccg ccc acc acc     1314
Gly Ser Pro Glu Pro Leu Val Leu His Glu Glu Thr Pro Pro Thr Thr
        235                 240                 245

agc agc gac tct gag gag gaa caa gaa gat gag gaa gaa atc gat gtt     1362
Ser Ser Asp Ser Glu Glu Glu Gln Glu Asp Glu Glu Glu Ile Asp Val
    250                 255                 260

gtt tct gtg gaa aag agg cag gct cct ggc aaa agg tca gag tct gga     1410
Val Ser Val Glu Lys Arg Gln Ala Pro Gly Lys Arg Ser Glu Ser Gly
265                 270                 275                 280

tca cct tct gct gga ggc cac agc aaa cct cct cac agc cca ctg gtc     1458
Ser Pro Ser Ala Gly Gly His Ser Lys Pro Pro His Ser Pro Leu Val
                285                 290                 295

ctc aag agg tgc cac gtc tcc aca cat cag cac aac tac gca gcg cct     1506
Leu Lys Arg Cys His Val Ser Thr His Gln His Asn Tyr Ala Ala Pro
            300                 305                 310

ccc tcc act cgg aag gac tat cct gct gcc aag agg gtc aag ttg gac     1554
Pro Ser Thr Arg Lys Asp Tyr Pro Ala Ala Lys Arg Val Lys Leu Asp
        315                 320                 325

agt gtc aga gtc ctg aga cag atc agc aac aac cga aaa tgc acc agc     1602
Ser Val Arg Val Leu Arg Gln Ile Ser Asn Asn Arg Lys Cys Thr Ser
    330                 335                 340

ccc agg tcc tcg gac acc gag gag aat gtc aag agg cga aca cac aac     1650
Pro Arg Ser Ser Asp Thr Glu Glu Asn Val Lys Arg Arg Thr His Asn
345                 350                 355                 360

gtc ttg gag cgc cag agg agg aac gag cta aaa cgg agc ttt ttt gcc     1698
Val Leu Glu Arg Gln Arg Arg Asn Glu Leu Lys Arg Ser Phe Phe Ala
                365                 370                 375

ctg cgt gac cag atc ccg gag ttg gaa aac aat gaa aag gcc ccc aag     1746
Leu Arg Asp Gln Ile Pro Glu Leu Glu Asn Asn Glu Lys Ala Pro Lys
            380                 385                 390

gta gtt atc ctt aaa aaa gcc aca gca tac atc ctg tcc gtc caa gca     1794
Val Val Ile Leu Lys Lys Ala Thr Ala Tyr Ile Leu Ser Val Gln Ala
        395                 400                 405

gag gag caa aag ctc att tct gaa gag gac ttg ttg cgg aaa cga cga     1842
Glu Glu Gln Lys Leu Ile Ser Glu Glu Asp Leu Leu Arg Lys Arg Arg
    410                 415                 420

gaa cag ttg aaa cac aaa ctt gaa cag cta cgg aac tct tgt gcg taa     1890
Glu Gln Leu Lys His Lys Leu Glu Gln Leu Arg Asn Ser Cys Ala
425                 430                 435
```

```
ggaaaagtaa ggaaaacgat tccttctaac agaaatgtcc tgagcaatca cctatgaact   1950

tgtttcaaat gcatgatcaa atgcaacctc acaaccttgg ctgagtcttg agactgaaag   2010

atttagccat aatgtaaact gcctcaaatt ggactttggg cataaaagaa cttttttatg   2070

cttaccatct tttttttttc tttaacagat ttgtatttaa gaattgtttt taaaaaattt   2130

taagatttac acaatgtttc tctgtaaata ttgccattaa atgtaaataa ctttaataaa   2190

acgtttatag cagttacaca gaatttcaat cctagtatat agtacctagt attataggta   2250

ctataaaccc taattttttt tatttaagta cattttgctt tttaaagttg atttttttct   2310

attgttttta gaaaaaataa aataactggc aaatatatca ttgagccaaa tcttaaaaaa   2370

aaaaaaaaa                                                           2379
```

```
<210> SEQ ID NO 2
<211> LENGTH: 439
<212> TYPE: PRT
<213> ORGANISM: Homo Sapience

<400> SEQUENCE: 2

Met Pro Leu Asn Val Ser Phe Thr Asn Arg Asn Tyr Asp Leu Asp Tyr
1               5                   10                  15

Asp Ser Val Gln Pro Tyr Phe Tyr Cys Asp Glu Glu Glu Asn Phe Tyr
            20                  25                  30

Gln Gln Gln Gln Gln Ser Glu Leu Gln Pro Pro Ala Pro Ser Glu Asp
        35                  40                  45

Ile Trp Lys Lys Phe Glu Leu Leu Pro Thr Pro Pro Leu Ser Pro Ser
    50                  55                  60

Arg Arg Ser Gly Leu Cys Ser Pro Ser Tyr Val Ala Val Thr Pro Phe
65                  70                  75                  80

Ser Leu Arg Gly Asp Asn Asp Gly Gly Gly Gly Ser Phe Ser Thr Ala
                85                  90                  95

Asp Gln Leu Glu Met Val Thr Glu Leu Leu Gly Gly Asp Met Val Asn
            100                 105                 110

Gln Ser Phe Ile Cys Asp Pro Asp Asp Glu Thr Phe Ile Lys Asn Ile
        115                 120                 125

Ile Ile Gln Asp Cys Met Trp Ser Gly Phe Ser Ala Ala Ala Lys Leu
    130                 135                 140

Val Ser Glu Lys Leu Ala Ser Tyr Gln Ala Ala Arg Lys Asp Ser Gly
145                 150                 155                 160

Ser Pro Asn Pro Ala Arg Gly His Ser Val Cys Ser Thr Ser Ser Leu
                165                 170                 175

Tyr Leu Gln Asp Leu Ser Ala Ala Ala Ser Glu Cys Ile Asp Pro Ser
            180                 185                 190

Val Val Phe Pro Tyr Pro Leu Asn Asp Ser Ser Ser Pro Lys Ser Cys
        195                 200                 205

Ala Ser Gln Asp Ser Ser Ala Phe Ser Pro Ser Ser Asp Ser Leu Leu
    210                 215                 220

Ser Ser Thr Glu Ser Ser Pro Gln Gly Ser Pro Glu Pro Leu Val Leu
225                 230                 235                 240

His Glu Glu Thr Pro Pro Thr Thr Ser Ser Asp Ser Glu Glu Glu Gln
                245                 250                 255

Glu Asp Glu Glu Glu Ile Asp Val Val Ser Val Glu Lys Arg Gln Ala
            260                 265                 270

Pro Gly Lys Arg Ser Glu Ser Gly Ser Pro Ser Ala Gly Gly His Ser
```

```
        275                 280                 285

Lys Pro Pro His Ser Pro Leu Val Leu Lys Arg Cys His Val Ser Thr
    290                 295                 300

His Gln His Asn Tyr Ala Ala Pro Pro Ser Thr Arg Lys Asp Tyr Pro
305                 310                 315                 320

Ala Ala Lys Arg Val Lys Leu Asp Ser Val Arg Val Leu Arg Gln Ile
                325                 330                 335

Ser Asn Asn Arg Lys Cys Thr Ser Pro Arg Ser Ser Asp Thr Glu Glu
            340                 345                 350

Asn Val Lys Arg Arg Thr His Asn Val Leu Glu Arg Gln Arg Arg Asn
        355                 360                 365

Glu Leu Lys Arg Ser Phe Phe Ala Leu Arg Asp Gln Ile Pro Glu Leu
    370                 375                 380

Glu Asn Asn Glu Lys Ala Pro Lys Val Val Ile Leu Lys Lys Ala Thr
385                 390                 395                 400

Ala Tyr Ile Leu Ser Val Gln Ala Glu Glu Gln Lys Leu Ile Ser Glu
                405                 410                 415

Glu Asp Leu Leu Arg Lys Arg Arg Glu Gln Leu Lys His Lys Leu Glu
            420                 425                 430

Gln Leu Arg Asn Ser Cys Ala
        435


<210> SEQ ID NO 3
<211> LENGTH: 2613
<212> TYPE: DNA
<213> ORGANISM: Homo Sapiens
<220> FEATURE:
<221> NAME/KEY: CDS
<222> LOCATION: (301)..(1695)

<400> SEQUENCE: 3

gtcatctgtc tggacgcgct gggtggatgc ggggggctcc tgggaactgt gttggagccg      60

agcaagcgct agccaggcgc aagcgcgcac agactgtagc catccgagga cacccccgcc     120

cccccggccc acccggagac acccgcgcag aatcgcctcc ggatcccctg cagtcggcgg     180

gagtgttgga ggtcggcgcc ggcccccgcc ttccgcgccc cccacgggaa ggaagcaccc     240

ccggtattaa aacgaacggg gcggaaagaa gccctcagtc gccggccggg aggcgagccg     300

atg ccg agc tgc tcc acg tcc acc atg ccg ggc atg atc tgc aag aac       348
Met Pro Ser Cys Ser Thr Ser Thr Met Pro Gly Met Ile Cys Lys Asn
1               5                   10                  15

cca gac ctc gag ttt gac tcg cta cag ccc tgc ttc tac ccg gac gaa       396
Pro Asp Leu Glu Phe Asp Ser Leu Gln Pro Cys Phe Tyr Pro Asp Glu
            20                  25                  30

gat gac ttc tac ttc ggc ggc ccc gac tcg acc ccc ccg ggg gag gac       444
Asp Asp Phe Tyr Phe Gly Gly Pro Asp Ser Thr Pro Pro Gly Glu Asp
        35                  40                  45

atc tgg aag aag ttt gag ctg ctg ccc acg ccc ccg ctg tcg ccc agc       492
Ile Trp Lys Lys Phe Glu Leu Leu Pro Thr Pro Pro Leu Ser Pro Ser
    50                  55                  60

cgt ggc ttc gcg gag cac agc tcc gag ccc ccg agc tgg gtc acg gag       540
Arg Gly Phe Ala Glu His Ser Ser Glu Pro Pro Ser Trp Val Thr Glu
65                  70                  75                  80

atg ctg ctt gag aac gag ctg tgg ggc agc ccg gcc gag gag gac gcg       588
Met Leu Leu Glu Asn Glu Leu Trp Gly Ser Pro Ala Glu Glu Asp Ala
                85                  90                  95

ttc ggc ctg ggg gga ctg ggt ggc ctc acc ccc aac ccg gtc atc ctc       636
Phe Gly Leu Gly Gly Leu Gly Gly Leu Thr Pro Asn Pro Val Ile Leu
```

```
            100                 105                 110

cag gac tgc atg tgg agc ggc ttc tcc gcc cgc gag aag ctg gag cgc      684
Gln Asp Cys Met Trp Ser Gly Phe Ser Ala Arg Glu Lys Leu Glu Arg
        115                 120                 125

gcc gtg agc gag aag ctg cag cac ggc cgc ggg ccg cca acc gcc ggt      732
Ala Val Ser Glu Lys Leu Gln His Gly Arg Gly Pro Pro Thr Ala Gly
    130                 135                 140

tcc acc gcc cag tcc ccg gga gcc ggc gcc gcc agc cct gcg ggt cgc      780
Ser Thr Ala Gln Ser Pro Gly Ala Gly Ala Ala Ser Pro Ala Gly Arg
145                 150                 155                 160

ggg cac ggc ggg gct gcg gga gcc ggc cgc gcc ggg gcc gcc ctg ccc      828
Gly His Gly Gly Ala Ala Gly Ala Gly Arg Ala Gly Ala Ala Leu Pro
                165                 170                 175

gcc gag ctc gcc cac ccg gcc gcc gag tgc gtg gat ccc gcc gtg gtc      876
Ala Glu Leu Ala His Pro Ala Ala Glu Cys Val Asp Pro Ala Val Val
            180                 185                 190

ttc ccc ttt ccc gtg aac aag cgc gag cca gcg ccc gtg ccc gca gcc      924
Phe Pro Phe Pro Val Asn Lys Arg Glu Pro Ala Pro Val Pro Ala Ala
        195                 200                 205

ccg gcc agt gcc ccg gcg gcg ggc cct gcg gtc gcc tcg ggg gcg ggt      972
Pro Ala Ser Ala Pro Ala Ala Gly Pro Ala Val Ala Ser Gly Ala Gly
    210                 215                 220

att gcc gcc cca gcc ggg gcc ccg ggg gtc gcc cct ccg cgc cca ggc     1020
Ile Ala Ala Pro Ala Gly Ala Pro Gly Val Ala Pro Pro Arg Pro Gly
225                 230                 235                 240

ggc cgc cag acc agc ggc ggc gac cac aag gcc ctc agt acc tcc gga     1068
Gly Arg Gln Thr Ser Gly Gly Asp His Lys Ala Leu Ser Thr Ser Gly
                245                 250                 255

gag gac acc ctg agc gat tca gat gat gaa gat gat gaa gag gaa gat     1116
Glu Asp Thr Leu Ser Asp Ser Asp Asp Glu Asp Asp Glu Glu Glu Asp
            260                 265                 270

gaa gag gaa gaa atc gac gtg gtc act gtg gag aag cgg cgt tcc tcc     1164
Glu Glu Glu Glu Ile Asp Val Val Thr Val Glu Lys Arg Arg Ser Ser
        275                 280                 285

tcc aac acc aag gct gtc acc aca ttc acc atc act gtg cgt ccc aag     1212
Ser Asn Thr Lys Ala Val Thr Thr Phe Thr Ile Thr Val Arg Pro Lys
    290                 295                 300

aac gca gcc ctg ggt ccc ggg agg gct cag tcc agc gag ctg atc ctc     1260
Asn Ala Ala Leu Gly Pro Gly Arg Ala Gln Ser Ser Glu Leu Ile Leu
305                 310                 315                 320

aaa cga tgc ctt ccc atc cac cag cag cac aac tat gcc gcc ccc tct     1308
Lys Arg Cys Leu Pro Ile His Gln Gln His Asn Tyr Ala Ala Pro Ser
                325                 330                 335

ccc tac gtg gag agt gag gat gca ccc cca cag aag aag ata aag agc     1356
Pro Tyr Val Glu Ser Glu Asp Ala Pro Pro Gln Lys Lys Ile Lys Ser
            340                 345                 350

gag gcg tcc cca cgt ccg ctc aag agt gtc atc ccc cca aag gct aag     1404
Glu Ala Ser Pro Arg Pro Leu Lys Ser Val Ile Pro Pro Lys Ala Lys
        355                 360                 365

agc ttg agc ccc cga aac tct gac tcg gag gac agt gag cgt cgc aga     1452
Ser Leu Ser Pro Arg Asn Ser Asp Ser Glu Asp Ser Glu Arg Arg Arg
    370                 375                 380

aac cac aac atc ctg gag cgc cag cgc cgc aac gac ctt cgg tcc agc     1500
Asn His Asn Ile Leu Glu Arg Gln Arg Arg Asn Asp Leu Arg Ser Ser
385                 390                 395                 400

ttt ctc acg ctc agg gac cac gtg ccg gag ttg gta aag aat gag aag     1548
Phe Leu Thr Leu Arg Asp His Val Pro Glu Leu Val Lys Asn Glu Lys
                405                 410                 415

gcc gcc aag gtg gtc att ttg aaa aag gcc act gag tat gtc cac tcc     1596
```

```
Ala Ala Lys Val Val Ile Leu Lys Lys Ala Thr Glu Tyr Val His Ser
            420                 425                 430

ctc cag gcc gag gag cac cag ctt ttg ctg gaa aag gaa aaa ttg cag     1644
Leu Gln Ala Glu Glu His Gln Leu Leu Leu Glu Lys Glu Lys Leu Gln
        435                 440                 445

gca aga cag cag cag ttg cta aag aaa att gaa cac gct cgg act tgc     1692
Ala Arg Gln Gln Gln Leu Leu Lys Lys Ile Glu His Ala Arg Thr Cys
    450                 455                 460

tag acgcttctca aaactggaca gtcactgcca ctttgcacat tttgattttt          1745

tttttaaaca aacattgtgt tgacattaag aatgttggtt tactttcaaa tcggtcccct   1805

gtcgagttcg gctctgggtg ggcagtagga ccaccagtgt ggggttctgc tgggaccttg   1865

gagagcctgc atcccaggat gctgggtggc cctgcagcct cctccacctc acctccatga   1925

cagcgctaaa cgttggtgac ggttgggagc ctctggggct gttgaagtca ccttgtgtgt   1985

tccaagtttc caaacaacag aaagtcattc cttcttttta aaatggtgct taagttccag   2045

cagatgccac ataaggggtt tgccatttga tacccctggg gaacatttct gtaaatacca   2105

ttgacacatc cgccttttgt atacatcctg ggtaatgaga ggtggctttt gcggccagta   2165

ttagactgga agttcatacc taagtactgt aataatacct caatgtttga ggagcatgtt   2225

ttgtatacaa atatattgtt aatctctgtt atgtactgta ctaattctta cactgcctgt   2285

atactttagt atgacgctga tacataacta aatttgatac ttatattttc gtatgaaaat   2345

gagttgtgaa agttttgagt agatattact ttatcacttt ttgaactaag aaacttttgt   2405

aaagaaattt actatatata tatgcctttt tcctagcctg tttcttcctg ttaatgtatt   2465

tgttcatgtt tggtgcatag aactgggtaa atgcaaagtt ctgtgtttaa tttcttcaaa   2525

atgtatatat ttagtgctgc atcttatagc actttgaaat acctcatgtt tatgaaaata   2585

aatagcttaa aattaaatga aaaaaaaa                                      2613


<210> SEQ ID NO 4
<211> LENGTH: 464
<212> TYPE: PRT
<213> ORGANISM: Homo Sapiens

<400> SEQUENCE: 4

Met Pro Ser Cys Ser Thr Ser Thr Met Pro Gly Met Ile Cys Lys Asn
1               5                   10                  15

Pro Asp Leu Glu Phe Asp Ser Leu Gln Pro Cys Phe Tyr Pro Asp Glu
            20                  25                  30

Asp Asp Phe Tyr Phe Gly Gly Pro Asp Ser Thr Pro Pro Gly Glu Asp
        35                  40                  45

Ile Trp Lys Lys Phe Glu Leu Leu Pro Thr Pro Pro Leu Ser Pro Ser
    50                  55                  60

Arg Gly Phe Ala Glu His Ser Ser Glu Pro Pro Ser Trp Val Thr Glu
65                  70                  75                  80

Met Leu Leu Glu Asn Glu Leu Trp Gly Ser Pro Ala Glu Glu Asp Ala
                85                  90                  95

Phe Gly Leu Gly Gly Leu Gly Gly Leu Thr Pro Asn Pro Val Ile Leu
            100                 105                 110

Gln Asp Cys Met Trp Ser Gly Phe Ser Ala Arg Glu Lys Leu Glu Arg
        115                 120                 125

Ala Val Ser Glu Lys Leu Gln His Gly Arg Gly Pro Pro Thr Ala Gly
    130                 135                 140

Ser Thr Ala Gln Ser Pro Gly Ala Gly Ala Ala Ser Pro Ala Gly Arg
```

```
145                 150                 155                 160

Gly His Gly Gly Ala Ala Gly Ala Gly Arg Ala Gly Ala Ala Leu Pro
                165                 170                 175

Ala Glu Leu Ala His Pro Ala Ala Glu Cys Val Asp Pro Ala Val Val
            180                 185                 190

Phe Pro Phe Pro Val Asn Lys Arg Glu Pro Ala Pro Val Pro Ala Ala
        195                 200                 205

Pro Ala Ser Ala Pro Ala Ala Gly Pro Ala Val Ala Ser Gly Ala Gly
    210                 215                 220

Ile Ala Ala Pro Ala Gly Ala Pro Gly Val Ala Pro Pro Arg Pro Gly
225                 230                 235                 240

Gly Arg Gln Thr Ser Gly Gly Asp His Lys Ala Leu Ser Thr Ser Gly
                245                 250                 255

Glu Asp Thr Leu Ser Asp Ser Asp Asp Glu Asp Asp Glu Glu Glu Asp
            260                 265                 270

Glu Glu Glu Glu Ile Asp Val Val Thr Val Glu Lys Arg Arg Ser Ser
        275                 280                 285

Ser Asn Thr Lys Ala Val Thr Thr Phe Thr Ile Thr Val Arg Pro Lys
    290                 295                 300

Asn Ala Ala Leu Gly Pro Gly Arg Ala Gln Ser Ser Glu Leu Ile Leu
305                 310                 315                 320

Lys Arg Cys Leu Pro Ile His Gln Gln His Asn Tyr Ala Ala Pro Ser
                325                 330                 335

Pro Tyr Val Glu Ser Glu Asp Ala Pro Pro Gln Lys Lys Ile Lys Ser
            340                 345                 350

Glu Ala Ser Pro Arg Pro Leu Lys Ser Val Ile Pro Pro Lys Ala Lys
        355                 360                 365

Ser Leu Ser Pro Arg Asn Ser Asp Ser Glu Asp Ser Glu Arg Arg Arg
    370                 375                 380

Asn His Asn Ile Leu Glu Arg Gln Arg Arg Asn Asp Leu Arg Ser Ser
385                 390                 395                 400

Phe Leu Thr Leu Arg Asp His Val Pro Glu Leu Val Lys Asn Glu Lys
                405                 410                 415

Ala Ala Lys Val Val Ile Leu Lys Lys Ala Thr Glu Tyr Val His Ser
            420                 425                 430

Leu Gln Ala Glu Glu His Gln Leu Leu Leu Glu Lys Glu Lys Leu Gln
        435                 440                 445

Ala Arg Gln Gln Gln Leu Leu Lys Lys Ile Glu His Ala Arg Thr Cys
    450                 455                 460
```

<210> SEQ ID NO 5
<211> LENGTH: 3622
<212> TYPE: DNA
<213> ORGANISM: Homo Sapiens
<220> FEATURE:
<221> NAME/KEY: CDS
<222> LOCATION: (582)..(1676)

<400> SEQUENCE: 5

```
aatgcgcctg cagctcgcgc tcccgcgccg atcccgagag cgtccgggcc gccgtgcgcg      60

agcgagggag ggcgcgcgcg cgggggggc gcgcttgtga gtgcgggccg cgctctcggc      120

ggcgcgcatg tgcgtgtgtg ctggctgccg ggctgccccg agccggcggg gagccggtcc     180

gctccaggtg gcgggcggct ggagcgaggt gaggctgcgg gtggccaggg cacgggcgcg     240

ggtcccgcgg tgcgggctgg ctgcaggctg ccttctgggc acggcgcgcc cccgcccggc     300
```

```
cccgccgggc cctgggagct gcgctccggg cggcgctggc aaagtttgct ttgaactcgc    360

tgcccacagt cgggtccgcg cgctgcgatt ggcttcccct accactctga cccggggccc    420

ggcttcccgg gacgcgagga ctgggcgcag gctgcaagct ggtggggttg gggaggaacg    480

agagcccggc agccgactgt gccgagggac ccggggacac ctccttcgcc cggccggcac    540

ccggtcagca cgtccccct tccctcccgc agggagcgga c atg gac tac gac tcg    596
                                             Met Asp Tyr Asp Ser
                                             1               5

tac cag cac tat ttc tac gac tat gac tgc ggg gag gat ttc tac cgc    644
Tyr Gln His Tyr Phe Tyr Asp Tyr Asp Cys Gly Glu Asp Phe Tyr Arg
                10                  15                  20

tcc acg gcg ccc agc gag gac atc tgg aag aaa ttc gag ctg gtg cca    692
Ser Thr Ala Pro Ser Glu Asp Ile Trp Lys Lys Phe Glu Leu Val Pro
            25                  30                  35

tcg ccc ccc acg tcg ccg ccc tgg ggc ttg ggt ccc ggc gca ggg gac    740
Ser Pro Pro Thr Ser Pro Pro Trp Gly Leu Gly Pro Gly Ala Gly Asp
        40                  45                  50

ccg gcc ccc ggg att ggt ccc ccg gag ccg tgg ccc gga ggg tgc acc    788
Pro Ala Pro Gly Ile Gly Pro Pro Glu Pro Trp Pro Gly Gly Cys Thr
    55                  60                  65

gga gac gaa gcg gaa tcc cgg ggc cac tcg aaa ggc tgg ggc agg aac    836
Gly Asp Glu Ala Glu Ser Arg Gly His Ser Lys Gly Trp Gly Arg Asn
70                  75                  80                  85

tac gcc tcc atc ata cgc cgt gac tgc atg tgg agc ggc ttc tcg gcc    884
Tyr Ala Ser Ile Ile Arg Arg Asp Cys Met Trp Ser Gly Phe Ser Ala
                90                  95                  100

cgg gaa cgg ctg gag aga gct gtg agc gac cgg ctc gct cct ggc gcg    932
Arg Glu Arg Leu Glu Arg Ala Val Ser Asp Arg Leu Ala Pro Gly Ala
            105                 110                 115

ccc cgg ggg aac ccg ccc aag gcg tcc gcc gcc ccg gac tgc act ccc    980
Pro Arg Gly Asn Pro Pro Lys Ala Ser Ala Ala Pro Asp Cys Thr Pro
        120                 125                 130

agc ctc gaa gcc ggc aac ccg gcg ccc gcc gcc ccc tgt ccg ctg ggc   1028
Ser Leu Glu Ala Gly Asn Pro Ala Pro Ala Ala Pro Cys Pro Leu Gly
    135                 140                 145

gaa ccc aag acc cag gcc tgc tcc ggg tcc gag agc cca agc gac tcg   1076
Glu Pro Lys Thr Gln Ala Cys Ser Gly Ser Glu Ser Pro Ser Asp Ser
150                 155                 160                 165

gag aat gaa gaa att gat gtt gtg aca gta gag aag agg cag tct ctg   1124
Glu Asn Glu Glu Ile Asp Val Val Thr Val Glu Lys Arg Gln Ser Leu
                170                 175                 180

ggt att cgg aag ccg gtc acc atc acg gtg cga gca gac ccc ctg gat   1172
Gly Ile Arg Lys Pro Val Thr Ile Thr Val Arg Ala Asp Pro Leu Asp
            185                 190                 195

ccc tgc atg aag cat ttc cac atc tcc atc cat cag caa cag cac aac   1220
Pro Cys Met Lys His Phe His Ile Ser Ile His Gln Gln Gln His Asn
        200                 205                 210

tat gct gcc cgt ttt cct cca gaa agc tgc tcc caa gaa gag gct tca   1268
Tyr Ala Ala Arg Phe Pro Pro Glu Ser Cys Ser Gln Glu Glu Ala Ser
    215                 220                 225

gag agg ggt ccc caa gaa gag gtt ctg gag aga gat gct gca ggg gaa   1316
Glu Arg Gly Pro Gln Glu Glu Val Leu Glu Arg Asp Ala Ala Gly Glu
230                 235                 240                 245

aag gaa gat gag gag gat gaa gag att gtg agt ccc cca cct gta gaa   1364
Lys Glu Asp Glu Glu Asp Glu Glu Ile Val Ser Pro Pro Pro Val Glu
                250                 255                 260

agt gag gct gcc cag tcc tgc cac ccc aaa cct gtc agt tct gat act   1412
Ser Glu Ala Ala Gln Ser Cys His Pro Lys Pro Val Ser Ser Asp Thr
```

```
            265                 270                 275

gag gat gtg acc aag agg aag aat cac aac ttc ctg gag cgc aag agg     1460
Glu Asp Val Thr Lys Arg Lys Asn His Asn Phe Leu Glu Arg Lys Arg
        280                 285                 290

cgg aat gac ctg cgt tcg cga ttc ttg gcg ctg agg gac cag gtg ccc     1508
Arg Asn Asp Leu Arg Ser Arg Phe Leu Ala Leu Arg Asp Gln Val Pro
    295                 300                 305

acc ctg gcc agc tgc tcc aag gcc ccc aaa gta gtg atc cta agc aag     1556
Thr Leu Ala Ser Cys Ser Lys Ala Pro Lys Val Val Ile Leu Ser Lys
310                 315                 320                 325

gcc ttg gaa tac ttg caa gcc ctg gtg ggg gct gag aag agg atg gct     1604
Ala Leu Glu Tyr Leu Gln Ala Leu Val Gly Ala Glu Lys Arg Met Ala
                330                 335                 340

aca gag aaa aga cag ctc cga tgc cgg cag cag cag ttg cag aaa aga     1652
Thr Glu Lys Arg Gln Leu Arg Cys Arg Gln Gln Gln Leu Gln Lys Arg
            345                 350                 355

att gca tac ctc act ggc tac taa ctgaccaaaa agcctgacag ttctgtctta    1706
Ile Ala Tyr Leu Thr Gly Tyr
        360

cgaagacaca agtttatttt ttaacctccc tctccccttt agtaatttgc acattttggt   1766

tatggtggga cagtctggac agtagatccc agaatgcatt gcagccggtg cacacacaat   1826

aaaggcttgc attcttggaa accttgaaac ccagctctcc ctcttccctg actcatggga   1886

gtgctgtatg ttctctggcg cctttggctt cccagcaggc agctgactga ggagccttgg   1946

ggtctgccta gctcactagc tctgaagaaa aggctgacag atgctatgca acaggtggtg   2006

gatgttgtca ggggctccag cctgcatgaa atctcacact ctgcatgagc tttaggctag   2066

gaaaggatgc tcccaactgg tgtctctggg gtgatgcaag gacagctggg cctggatgct   2126

ctccctgagg ctccttttc cagaagacac acgagctgtc ttgggtgaag acaagcttgc    2186

agacttgatc aacattgacc attacctcac tgtcagacac tttacagtag ccaaggagtt   2246

ggaaaccttt atatattatg atgttagctg accccccttcc tcccactccc aatgctgcga  2306

ccctgggaac acttaaaaag cttggcctct agattctttg tctcagagcc ctctgggctc   2366

tctcctctga gggagggacc tttctttcct cacaagggac ttttttgttc cattatgcct   2426

tgttatgcaa tgggctctac agcacccttt cccacaggtc agaaatattt ccccaagaca   2486

cagggaaatc ggtcctagcc tggggcctgg ggatagcttg gagtcctggc ccatgaactt   2546

gatccctgcc caggtgtttt ccgaggggca cttgaggccc agtcttttct caaggcaggt   2606

gtaagacacc tcagagggag aactgtactg ctgcctcttt cccacctgcc tcatctcaat   2666

ccttgagcgg caagtttgaa gttcttctgg aaccatgcaa atctgtcctc ctcatgcaat   2726

tccaaggagc ttgctggctc tgcagccacc cttgggcccc ttccagcctg ccatgaatca   2786

gatatctttc ccagaatctg ggcgtttctg aagttttggg gagagctgtt gggactcatc   2846

cagtgctcca gaaggtggac ttgcttctgg tgggttttaa aggagcctcc aggagatatg   2906

cttagccaac catgatggat ttaccccag ctggactcgg cagctccaag tggaatccac    2966

gtgcagcttc tagtctggga aagtcaccca acctagcagt tgtcatgtgg gtaacctcag   3026

gcacctctaa gcctgtcctg gaagaaggac cagcagcccc tccagaactc tgcccaggac   3086

agcaggtgcc tgctggctct gggtttggaa gttggggtgg gtagggggtg gtaagtacta   3146

tatatggctc tggaaaacca gctgctactt ccaaatctat tgtccataat ggtttctttc   3206

tgaggttgct tcttggcctc agaggacccc aggggatgtt tggaaatagc ctctctaccc   3266

ttctggagca tggtttacaa aagccagctg acttctggaa ttgtctatgg aggacagttt   3326
```

```
gggtgtaggt tactgatgtc tcaactgaat agcttgtgtt ttataagctg ctgttggcta   3386

ttatgctggg ggagtctttt ttttttatat tgtatttttg tatgcctttt gcaaagtggt   3446

gttaactgtt tttgtacaag gaaaaaaact cttggggcaa tttcctgttg caagggtctg   3506

atttattttg aaaggcaagt tcacctgaaa ttttgtattt agttgtgatt actgattgcc   3566

tgattttaaa atgttgcctt ctgggacatc ttctaataaa agatttctca aacatg       3622


<210> SEQ ID NO 6
<211> LENGTH: 364
<212> TYPE: PRT
<213> ORGANISM: Homo Sapiens

<400> SEQUENCE: 6

Met Asp Tyr Asp Ser Tyr Gln His Tyr Phe Tyr Asp Tyr Asp Cys Gly
1               5                   10                  15

Glu Asp Phe Tyr Arg Ser Thr Ala Pro Ser Glu Asp Ile Trp Lys Lys
            20                  25                  30

Phe Glu Leu Val Pro Ser Pro Pro Thr Ser Pro Pro Trp Gly Leu Gly
        35                  40                  45

Pro Gly Ala Gly Asp Pro Ala Pro Gly Ile Gly Pro Pro Glu Pro Trp
    50                  55                  60

Pro Gly Gly Cys Thr Gly Asp Glu Ala Glu Ser Arg Gly His Ser Lys
65                  70                  75                  80

Gly Trp Gly Arg Asn Tyr Ala Ser Ile Ile Arg Arg Asp Cys Met Trp
                85                  90                  95

Ser Gly Phe Ser Ala Arg Glu Arg Leu Glu Arg Ala Val Ser Asp Arg
            100                 105                 110

Leu Ala Pro Gly Ala Pro Arg Gly Asn Pro Pro Lys Ala Ser Ala Ala
        115                 120                 125

Pro Asp Cys Thr Pro Ser Leu Glu Ala Gly Asn Pro Ala Pro Ala Ala
    130                 135                 140

Pro Cys Pro Leu Gly Glu Pro Lys Thr Gln Ala Cys Ser Gly Ser Glu
145                 150                 155                 160

Ser Pro Ser Asp Ser Glu Asn Glu Glu Ile Asp Val Val Thr Val Glu
                165                 170                 175

Lys Arg Gln Ser Leu Gly Ile Arg Lys Pro Val Thr Ile Thr Val Arg
            180                 185                 190

Ala Asp Pro Leu Asp Pro Cys Met Lys His Phe His Ile Ser Ile His
        195                 200                 205

Gln Gln Gln His Asn Tyr Ala Ala Arg Phe Pro Pro Glu Ser Cys Ser
    210                 215                 220

Gln Glu Glu Ala Ser Glu Arg Gly Pro Gln Glu Glu Val Leu Glu Arg
225                 230                 235                 240

Asp Ala Ala Gly Glu Lys Glu Asp Glu Glu Asp Glu Glu Ile Val Ser
                245                 250                 255

Pro Pro Pro Val Glu Ser Glu Ala Ala Gln Ser Cys His Pro Lys Pro
            260                 265                 270

Val Ser Ser Asp Thr Glu Asp Val Thr Lys Arg Lys Asn His Asn Phe
        275                 280                 285

Leu Glu Arg Lys Arg Arg Asn Asp Leu Arg Ser Arg Phe Leu Ala Leu
    290                 295                 300

Arg Asp Gln Val Pro Thr Leu Ala Ser Cys Ser Lys Ala Pro Lys Val
305                 310                 315                 320
```

```
Val Ile Leu Ser Lys Ala Leu Glu Tyr Leu Gln Ala Leu Val Gly Ala
                325                 330                 335

Glu Lys Arg Met Ala Thr Glu Lys Arg Gln Leu Arg Cys Arg Gln Gln
            340                 345                 350

Gln Leu Gln Lys Arg Ile Ala Tyr Leu Thr Gly Tyr
        355                 360


<210> SEQ ID NO 7
<211> LENGTH: 81
<212> TYPE: DNA
<213> ORGANISM: Foot-and-mouth disease virus

<400> SEQUENCE: 7

aaaattgtcg ctcctgtcaa acaaactctt aactttgatt tactcaaact ggctggggat     60

gtagaaagca atccaggtcc a                                               81


<210> SEQ ID NO 8
<211> LENGTH: 34
<212> TYPE: DNA
<213> ORGANISM: Bacteriophage P1

<400> SEQUENCE: 8

ataacttcgt atagcataca ttatacgaag ttat                                 34


<210> SEQ ID NO 9
<211> LENGTH: 34
<212> TYPE: DNA
<213> ORGANISM: Artificial
<220> FEATURE:
<223> OTHER INFORMATION: mutant loxP (lox71) sequence

<400> SEQUENCE: 9

taccgttcgt atagcataca ttatacgaag ttat                                 34


<210> SEQ ID NO 10
<211> LENGTH: 34
<212> TYPE: DNA
<213> ORGANISM: Artificial
<220> FEATURE:
<223> OTHER INFORMATION: mutant loxP (lox66) sequence

<400> SEQUENCE: 10

ataacttcgt atagcataca ttatacgaac ggta                                 34


<210> SEQ ID NO 11
<211> LENGTH: 30
<212> TYPE: DNA
<213> ORGANISM: Artificial
<220> FEATURE:
<223> OTHER INFORMATION: Synthetic primer

<400> SEQUENCE: 11

caccatgctc gactacgact cggtgcagcc                                      30


<210> SEQ ID NO 12
<211> LENGTH: 30
<212> TYPE: DNA
<213> ORGANISM: Artificial
<220> FEATURE:
<223> OTHER INFORMATION: Synthetic Primer

<400> SEQUENCE: 12

caccatgccc ccggcgccca gcgaggatat                                      30
```

```
<210> SEQ ID NO 13
<211> LENGTH: 30
<212> TYPE: DNA
<213> ORGANISM: Artificial
<220> FEATURE:
<223> OTHER INFORMATION: Synthetic Primer

<400> SEQUENCE: 13

caccatgcgc cgctccgggc tctgctcgcc                                        30


<210> SEQ ID NO 14
<211> LENGTH: 30
<212> TYPE: DNA
<213> ORGANISM: Artificial
<220> FEATURE:
<223> OTHER INFORMATION: Synthetic Primer

<400> SEQUENCE: 14

caccatgcgg ggagacaacg acggcggtgg                                        30


<210> SEQ ID NO 15
<211> LENGTH: 30
<212> TYPE: DNA
<213> ORGANISM: Artificial
<220> FEATURE:
<223> OTHER INFORMATION: Synthetic Primer

<400> SEQUENCE: 15

caccatggga gacatggtga accagagttt                                        30


<210> SEQ ID NO 16
<211> LENGTH: 30
<212> TYPE: DNA
<213> ORGANISM: Artificial
<220> FEATURE:
<223> OTHER INFORMATION: Synthetic Primer

<400> SEQUENCE: 16

caccatgatc atcatccagg actgtatgtg                                        30


<210> SEQ ID NO 17
<211> LENGTH: 30
<212> TYPE: DNA
<213> ORGANISM: Artificial
<220> FEATURE:
<223> OTHER INFORMATION: Synthetic Primer

<400> SEQUENCE: 17

caccatggcc gccaagctcg tctcagagaa                                        30


<210> SEQ ID NO 18
<211> LENGTH: 30
<212> TYPE: DNA
<213> ORGANISM: Artificial
<220> FEATURE:
<223> OTHER INFORMATION: Synthetic Primer

<400> SEQUENCE: 18

tcacgcacaa gagttccgta gctgttcaag                                        30


<210> SEQ ID NO 19
<211> LENGTH: 25
<212> TYPE: DNA
<213> ORGANISM: Artificial
<220> FEATURE:
<223> OTHER INFORMATION: Synthetic Primer
```

<400> SEQUENCE: 19
caggactgta tggagagcgg tttct 25

<210> SEQ ID NO 20
<211> LENGTH: 25
<212> TYPE: DNA
<213> ORGANISM: Artificial
<220> FEATURE:
<223> OTHER INFORMATION: Synthetic Primer

<400> SEQUENCE: 20
agaaaccgct ctccatacag tcctg 25

<210> SEQ ID NO 21
<211> LENGTH: 30
<212> TYPE: DNA
<213> ORGANISM: Artificial
<220> FEATURE:
<223> OTHER INFORMATION: Synthetic Primer

<400> SEQUENCE: 21
caccatgtcc acggcgccca gcgaggacat 30

<210> SEQ ID NO 22
<211> LENGTH: 30
<212> TYPE: DNA
<213> ORGANISM: Artificial
<220> FEATURE:
<223> OTHER INFORMATION: Synthetic Primer

<400> SEQUENCE: 22
caccatgtgg ggcttgggtc ccggcgcagg 30

<210> SEQ ID NO 23
<211> LENGTH: 30
<212> TYPE: DNA
<213> ORGANISM: Artificial
<220> FEATURE:
<223> OTHER INFORMATION: Synthetic Primer

<400> SEQUENCE: 23
caccatggga gacgaagcgg aatcccgggg 30

<210> SEQ ID NO 24
<211> LENGTH: 30
<212> TYPE: DNA
<213> ORGANISM: Artificial
<220> FEATURE:
<223> OTHER INFORMATION: Synthetic Primer

<400> SEQUENCE: 24
caccatgatc atacgccgtg actgcatgtg 30

<210> SEQ ID NO 25
<211> LENGTH: 30
<212> TYPE: DNA
<213> ORGANISM: Artificial
<220> FEATURE:
<223> OTHER INFORMATION: Synthetic Primer

<400> SEQUENCE: 25
caccatgcgg gaacggctgg agagagctgt 30

<210> SEQ ID NO 26

```
<211> LENGTH: 26
<212> TYPE: DNA
<213> ORGANISM: Artificial
<220> FEATURE:
<223> OTHER INFORMATION: Sythetic Primer

<400> SEQUENCE: 26

ttagtagcca gtgaggtatg caattc                                          26
```